United States Patent [19]
Yamada et al.

[11] Patent Number: 5,369,096
[45] Date of Patent: Nov. 29, 1994

[54] GLYCOLIPID DERIVATIVES

[75] Inventors: Yutaka Yamada; Naofumi Takahashi; Keisuke Adachi; Akihiko Kameyama, all of Yokohama, Japan

[73] Assignee: The Nisshin Oil Mills, Ltd., Tokyo, Japan

[21] Appl. No.: 91,252

[22] Filed: Jul. 15, 1993

[30] Foreign Application Priority Data

Jul. 15, 1992 [JP] Japan .................. 4-188001

[51] Int. Cl.$^5$ ............................................. A61K 31/72
[52] U.S. Cl. ....................................... 514/61; 514/54; 536/17.4
[58] Field of Search ................. 514/54, 61; 536/17.4

[56] References Cited

U.S. PATENT DOCUMENTS

| | | | |
|---|---|---|---|
| 4,762,800 | 8/1988 | Rettig et al. | 436/548 |
| 5,002,759 | 3/1991 | Gaffar et al. | 424/49 |
| 5,143,712 | 9/1992 | Brandley et al. | 424/1.1 |

FOREIGN PATENT DOCUMENTS

| | | |
|---|---|---|
| 0069678 | 1/1983 | European Pat. Off. |
| WO91/19501 | 12/1991 | WIPO |
| WO91/19502 | 12/1991 | WIPO |
| WO92/02527 | 2/1992 | WIPO |
| WO92/07572 | 5/1992 | WIPO |

OTHER PUBLICATIONS

Akihiko Kameyama, et al., Synthetic Studies on Sialoglycoconjugates 22: Total Synthesis of Tumor-Associated Ganglioside, Sialyl Lewis X1, Journal of Carbohydrate Chemistry, 10 pp. 549-560 1991.

Fumito Yamazaki, et al., Synthesis of alpha-D-MANp-(1->3)-[beta-D-GlcpNAc-(1->4)]-[alpha-D-MANp-(1->6)]-beta-D-MANp-(1->4)-beta-D-GlcpNAc-(1->4)-[alpha-L-Fucp-(1->6)]-D-GlcpNAc, A Core Glycoheptaose of a "Bisected" Complex-Type Glycan of Glycoproteins Carbohydrate Research, 201. pp. 31-50. Jul. 17, 1989.

Takatoshi Murase, et al., A Facile, Regio- and Stereo-Selective Synthesis of Ganglioside GM Carbohydrate Research 188 pp. 71-80 1989.

Akiko Takada, et al. Contribution of Carbohydrate Antigens Sialyl Lewis A and Silyl Lewis X to Adhesion of Human Cancer Cells to Vscular Endo Thelium Cancer Research 53: pp. 354-361 Jan. 15, 1993.

Proc. Natl. Acad. Sci. USA, vol. 88, Nov. 1991, pp. 10372-10376, David Tyrrell, et al., "Structural Requirements for the Carbohydrate Ligand of E-Selectin".

Primary Examiner—John W. Rollins
Assistant Examiner—Kathleen Kahler Fonda
Attorney, Agent, or Firm—Oblon, Spivak, McClelland, Maier & Neustadt

[57] ABSTRACT

Disclosed are glycolipid derivatives of formula (I)

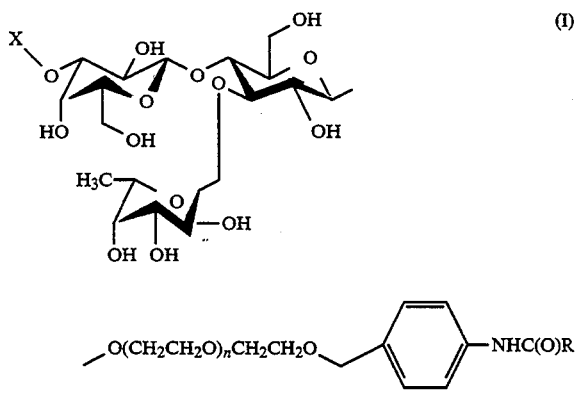

wherein X is a group selected from

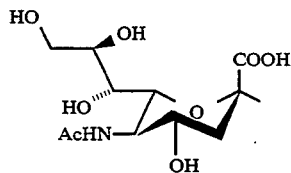

and

-continued
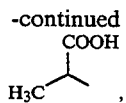
n is 0 or an integer of 1–10 and R denotes a branched hydrocarbon chain containing from 19 to 39 carbon atoms. Those compounds are useful as antiinflammatory agents, or as agents for the treatment of rheumatoid arthritis.
5 Claims, No Drawings

GLYCOLIPID DERIVATIVES

FIELD OF THE INVENTION

This invention relates to new glycolipid derivatives useful as a ligand which binds to an endothelial leukocyte adhesion molecule-1 (ELAM-1), processes for preparing the same and pharmaceutical compositions comprising such derivatives as an active ingredient. More particularly, it is concerned with a medicament which reduces or inhibits inflammation or inhibits hematogenous metastasis of cancers by suppressing the action of ELAM-1.

BACKGROUND OF THE INVENTION

In recent years, an attention has been invited to relation between cell adhesion proteins and the carbohydrate chain. Selectins including ELAM-1, GMP-140 and LECAM-1 are a cell adhesion protein which has a lectin-like domain, an EGF-like domain and a complement binding protein-like domain successively from the N terminus and a receptor of general class. These cell surface receptors are expressed on a variety of cells. ELAM-1 is an adhesion protein which is expressed on vascular endothelium and is bound to the carbohydrate chain ligand on the side of leukocyte. ELAM-1 is thought to be temporarily expressed on the blood vessel at the site of inflammation when stimulated by an inflammatory cytokines of IL-1 or the like, which plays a role of collecting the leukocytes and helping their migration to the site of lesion. Further, it was recently clarified that the ligand carbohydrate chain was expressed on cancer cells, and ELAM-1 is thought to be involved in hematogenous metastasis of cancers (Takada A. et al. Cancer Res. 53: 354–361, 1993).

Now, various approaches have been suggested to prevent inflammation and cancer metastasis by blocking the action of selectins and thus inhibiting cellular adhesion.

WO 91/19501 (published on Dec. 6, 1991) discloses a method for reducing or treating inflammation and other pathological symptoms which are mediated by intercellular adhesion, by using a compound having an oligosaccharide moiety containing fucose and sialic acid, as a ligand binding to selectin.

WO 91/19502 (published on Dec. 26, 1991) discloses compounds having the selectin-binding moiety of the general formula, $R_1$-Gal$\beta$1,4(Fuc$\alpha$1,3)GlcNAc-$(R_2)_a$, wherein $R_1$ is an oligosaccharide or $R_3$-$R_4$—C(-$CO_2H$)—, $R_3$ and $R_4$ are the same or different and each is H, $C_1$-$C_8$ alkyl, hydroxyl $C_1$-$C_8$ alkyl, aryl $C_1$-$C_8$ alkyl or alkoxy $C_1$-$C_8$ alkyl; and $R_2$ is $\beta$1, 3Gal, $\alpha$1, 2Man or $\alpha$1, 6GalNac; and a is 0 or 1.

WO 92/02527 (published on Feb. 20, 1992) discloses the compounds, as a ligand binding to ELAM-1, of the general formula In the formula, each of the saccharide rings shown is connected at its 1-position to the next saccharide ring at its 3-position or 4-position and wherein the variables are defined as follows:

At least one of A and B is

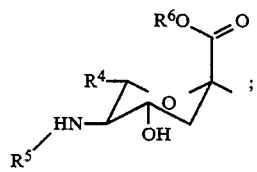

and the other is H, wherein $R^4$ is —(CHOH)$_3$H, H, alkyl containing 1 to 6 carbons, CHO, or perfluoroalkyl containing 1 to 6 carbons;

$R^5$ is selected from the group consisting of H, alkyl containing 1 to 6 carbons, COCH$_3$, COCH$_2$OH, COCF$_3$; and $R^6$ is selected from the group consisting of H, and an alkyl containing 1 to 6 carbons;

each D is independently H, a galactosyl or fucosyl wherein at least one D is $\alpha$-fucosyl connected to the 3-position or 4-position of the sugar to which it is bound;

each $R^3$ is independently OH or NAc;

n is an integer of from 0 to 10 with the proviso that if n is 0 and F is H, $R^3$ is OH;

F is H, a ceramide residue, or comprises a linking group or a solid support or a pharmaceutically active drug;

X is selected from the group consisting of O, S and NR$^6$ and in the saccharide at the reducing terminus, X may also represent the corresponding dicarbinol at C-1 and C-5.

Recently, ligand carbohydrate chains having different properties were discovered from the difference in the constituent carbohydrate residues other than sialic acid and Le$^x$ hapten portions in sialyl Le$^x$ carbohydrate chain, that is, variations in the O-glycoside bonded carbohydrate chain and the N-glycoside bonded carbohydrate chain of the glycolipids and glycoproteins. Thus, it has been becoming known that a series of these; sialyl Le$^x$ variants are also of a delicately different physiological significance.

With the elucidation of the ligand-receptor interaction it will be possible to develop compounds which inhibit selectin-mediated cellular adhesion which is useful in therapeutic regimens.

SUMMARY OF THE INVENTION

The present inventors have investigated a large number of glycolipid derivatives and have been successful in introducing an ethylene glycol unit terminated with an amino benzyl alcohol group into The carbohydrate chain of polysaccharides to prepare glycolipid deriva-

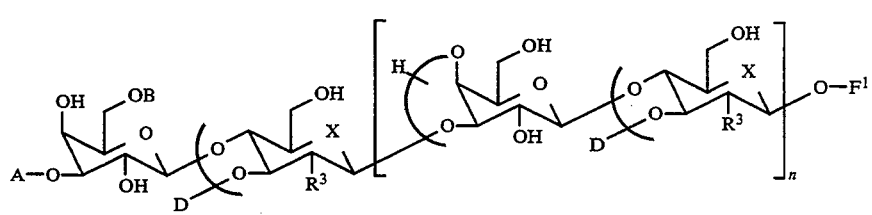

tives with superior hydrophilic-lipophilic balance as a ligand which binds to ELAM-1.

It is therefore an object of the invention to provide new glycolipid derivatives useful as a ligand binding to ELAM-1.

Another object of the invention is to provide pharmaceutical compositions useful for the treatment of inflammation, rheumatoid arthritis and like diseases which comprise new glycolipid derivatives as an ELAM-1 ligand.

A further object of the invention is to provide pharmaceutical compositions useful for inhibiting hematogenous metastasis of cancers which comprise new glycolipid derivatives as an ELAM-1 ligand.

A still further object of the invention is to provide processes for the preparation of new glycolipid derivatives and intermediates therefor.

DETAILED DESCRIPTION OF THE INVENTION

According to the invention there are provided glycolipid derivatives of formula (I)

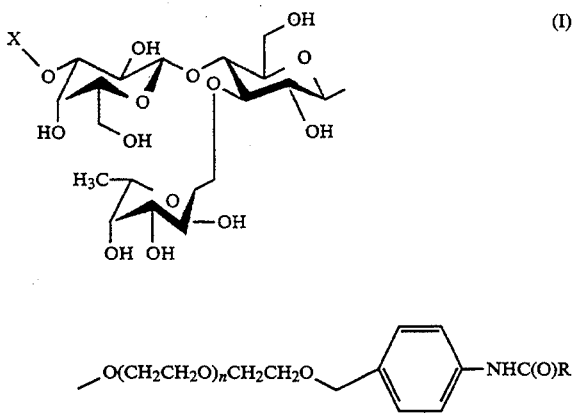

wherein X is a group selected from

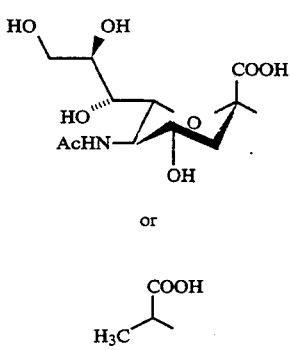

or n is 0 or an integer of 1–10 and R denotes a branched hydrocarbon chain containing from 19 to 39 carbon atoms.

The radical represented by RC(O) in formula (I) is a radical of a branched fatty acid containing from 20 to 40 carbon atoms. The corresponding fatty acids can include 2-hexyltetradecanoic acid, 2-octyltetradecanoic acid, 2-decyltetradecanoic acid, 2-dodecyltetradecanoic acid, 2-dodecylhexadecanoic acid, 2-dodecyloctadecanoic acid, 2-dodecyleicosanoic acid, 2-tetradecylhexadecanoic acid, 2-tetradecyloctadecanoic acid, 2-tetradecyleicosanoic acid, 2-hexadecyloctadecanoic acid, 2-hexadecyleicosanoic acid, 2-octadecyleicosanoic acid, 3-hexyltetradecanoic acid, 3-octyltetradecanoic acid, 3-decyltetradecanoic acid, 3-dodecyltetradecanoic acid, 3-dodecylhexadecanoic acid, 3-dodecyloctadecanoic acid, 3-dodecyleicosanoic acid, 3-tetradecylhexadecanoic acid, 3-tetradecyloctadecanoic acid, 3-tetradecyleicosanoic acid, 3-hexadecyloctadecanoic acid, 3-hexadecyleicosanoic acid, 3-octadecyleicosanoic acid and the like.

With reference to reaction schemes, preparation of the compounds of formula (I) and their intermediates will be illustrated below. The abbreviations used in the reaction schemes and the following descriptions have the following meanings.

Ac: Acetyl
Me: Methyl
Et: Ethyl
Ph: Phenyl
Bn: Benzyl
MPM: Methoxybenzyl
Bz: Benzoyl
SE: 2-Trimethylsilylethyl
Tf: Trifluoromethanesulfonyl
CPA: 2-chlorolactic acid
DBU: 1,8-Diazabicyclo-[5.4.0]-7-undecene
DMAP: Dimethylaminopyridine
DMF: Dimethylformamide
DMP: 1,3-Dimethoxypropane
DMTST: Dimethyl methylthiosulfonium trifluoromethanesulfonate
MS: Molecular sieves
NIS N-Iodosuccinimide
PTS: p-Toluenesulfonic acid
TBAB: Tetrabutylammonium bromide
TFA: Trifluoroacetic acid
WSC 1-Ethyl-3-(dimethylaminopropyl)carbodiimide, hydrochloride Preparation of the compounds of formula (I) (specifically, compound (5)) starting from a trisaccharide or tetrasaccharide derivative (specifically, compound (1)) and ethylene glycol derivatives (specifically, compound (3)) will be illustrated by Reaction Scheme 1.

REACTION SCHEME 1

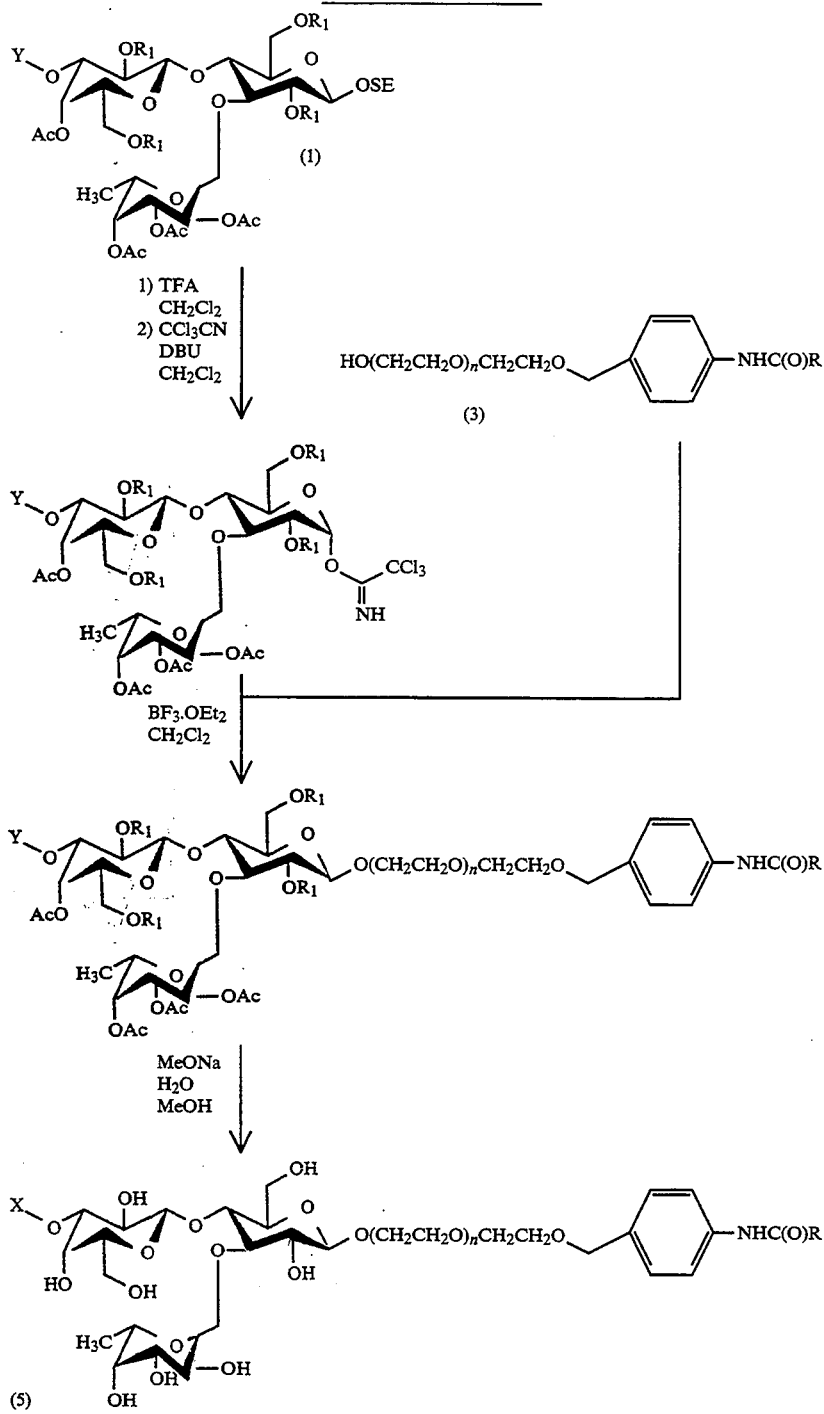

In Reaction Scheme 1, X, n and R are as defined above, $R_1$ denotes Ac or Bz and Y denotes the following:

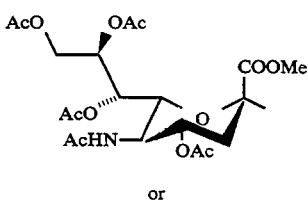

or

-continued

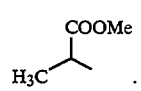

The SE group in compound (1) having hydroxy groups protected by a suitable protecting group is selectively removed with TFA followed by imidation with, e.g., trichloroacetonitrile in the presence of DBU to give compound (2) as a sugar donor. Then, condensation of compound (2) with compound (3) prepared as described below in the presence of a catalytic amount of BF$_3$.OEt$_2$ affords compound (4) with a lipid moiety introduced. Subsequently, the acyl protective groups on hydroxy groups are removed by transesterification e.g. in methanol using sodium methoxide as a catalyst. Finally, the methyl group that protects carboxyl groups is removed by hydrolysis to give compound (5) of the invention.

Purification of the compounds (intermediates) formed in the process steps and the objective compound is accomplished by the widely employed column chromatography on silica gel. All the compounds in this invention are purified by this technique, unless otherwise indicated.

Compound (3) which constitutes the lipid moiety is prepared, for example, by the reaction steps shown in Reaction Scheme 2 below.

REACTION SCHEME 2
HO(CH$_2$CH$_2$O)$_n$CH$_2$CH$_2$OH (6)   NO$_2$BnBr
      Ag$_2$O
      Benzene

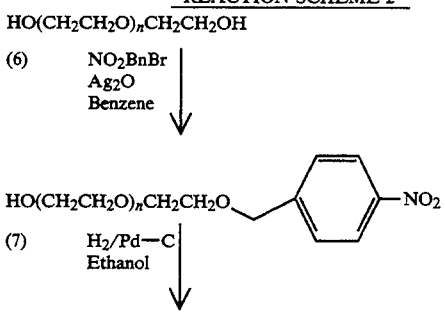

(7)   H$_2$/Pd—C
      Ethanol

-continued
REACTION SCHEME 2

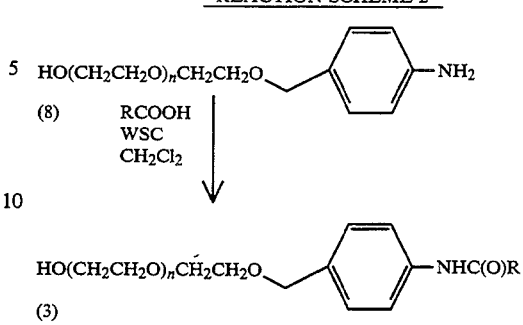

(8)   RCOOH
      WSC
      CH$_2$Cl$_2$

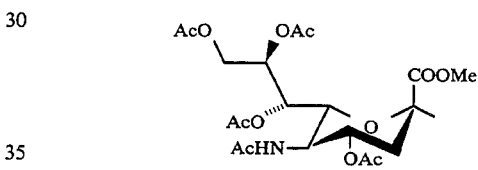

(3)

The starting material, ethylene glycol or polyethylene glycol (compound (6)) is reacted with an equimolar amount of nitrobenzyl bromide in the presence of a silver oxide catalyst to give a mononitrobenzyl ether compound (7) o The nitro group of compound (7) is converted to an amino group by catalytic reduction using a palladium/carbon catalyst to afford compound (8). Subsequent amidation with a fatty acid activated by C terminal activation with a carbodiimide extensively used in the peptide synthesis yields compound (3).

A compound of the starting materials in the reaction steps shown in Reaction Scheme 1, e.g., compound (1) where in Y is

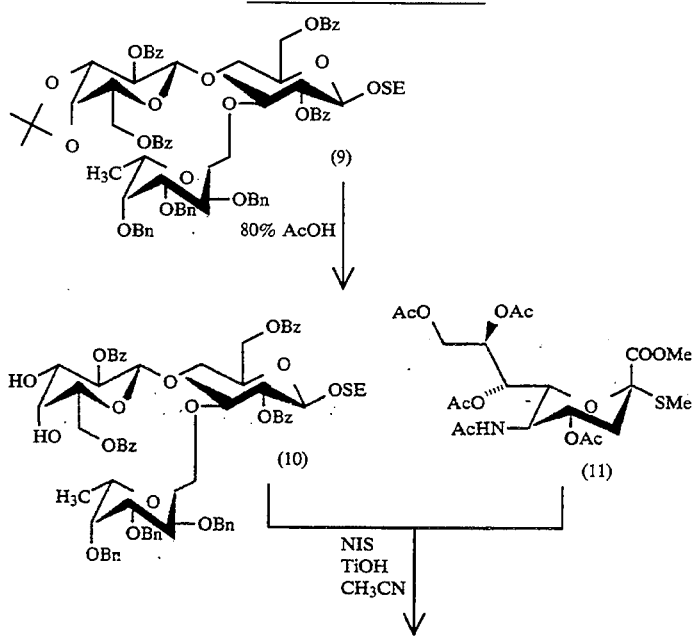

and R$_1$ is Bz can be prepared, for example, by the reaction steps shown in Reaction Scheme 3 below.

REACTION SCHEME 3

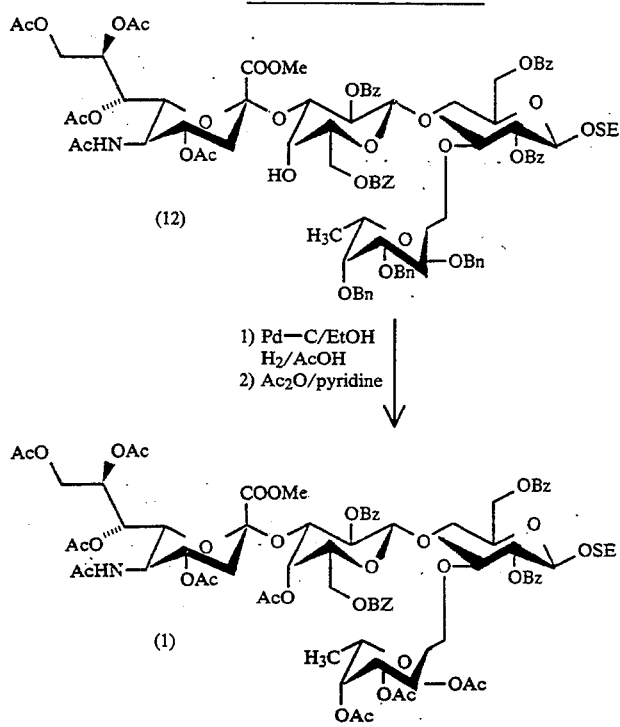

Thus, the isopropylidene group incorporated between 4- and 6-positions in the galactose of a trisaccharide compound (9) is removed under an acid condition with acetic acid to give compound (10) as a sugar acceptor.

Compound (11), a sugar donor known as compound 5 in T. Murase, A. Hasegawa et al., Carbohydrate Research, 188, 71–80, 1989 and compound (10) are dissolved, e.g., in acetonitrile and thoroughly dehydrated using molecular sieves 3A. The subsequent condensation in the presence of NIS and TfOH at a temperature of around −40° C. affords compound (12) in which a sialic acid is regio- and stereo-selectively introduced. Three Bn groups present in compound (12) are removed by catalytic reduction using a palladium/carbon catalyst. Subsequent acetylation of the free hydroxy groups with acetic anhydride and pyridine, provides compound (1) wherein Y is

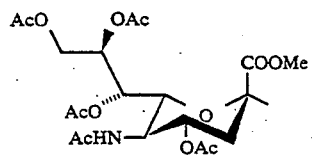

and $R_1$ is Bz.

In addition, compound (1) wherein Y is

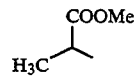

and $R_1$ is Ac can be prepared by the reaction steps shown in Reaction Schemes 4 and 5, below.

REACTION SCHEME 4

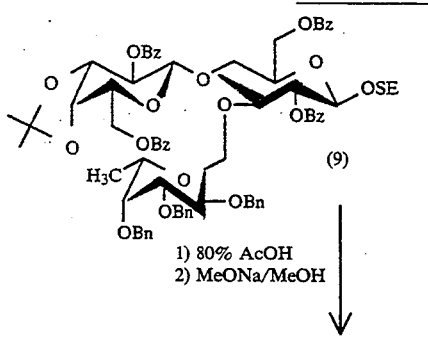

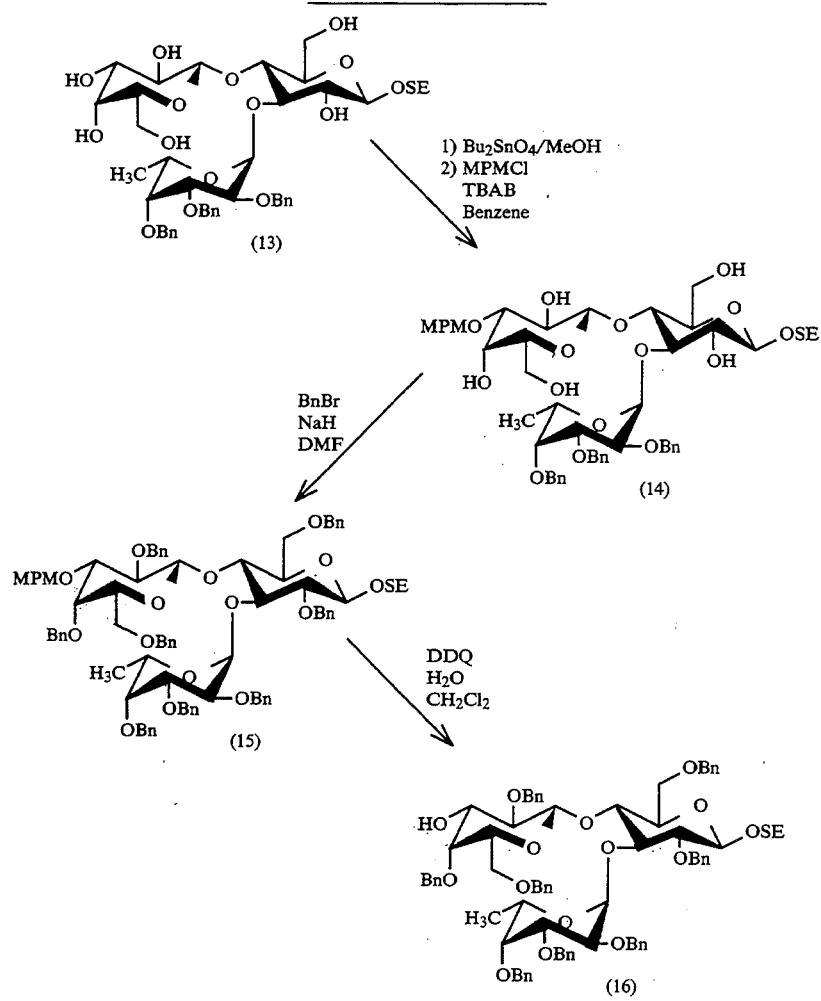
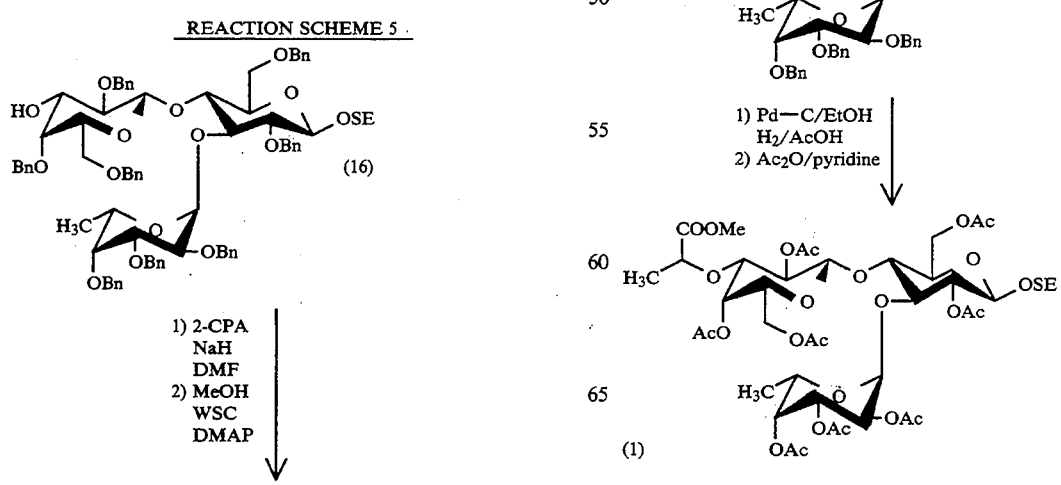

Starting from compound (9), the isopropyridene group between 4- and 6-positions on the galactose is removed in the above manner, followed by transesterification, e.g., in methanol using sodium methoxide as a catalyst to give compound (13) in which the acyl protective groups are removed. Between the free hydroxy groups on the galactose of compound (13) is reacted dibutyltin oxide (IV) to form a tin complex. The tin complex is reacted with methoxybenzyl chloride using TBAB as a catalyst to give compound (14) which was selectively protected at 3-position on the galactose. The remaining free hydroxy groups in compound (14) are converted with sodium hydride to the alkoxides. The alkoxides are reacted with benzyl bromide to give compound (15) followed by oxidative removal of the MPM group in a DDQ-water system, thus providing compound (16) containing a free hydroxyl group only at the 3-position of the galactose. The free hydroxyl group of compound (16) is converted with sodium hydride to the alkoxide which is then reacted with 2-chlorolactic acid followed by esterification using, e.g., WSC, DMAP and methanol to give compound (17). Removal of eight Bn groups of compound (17) by catalytic reduction with a palladium/carbon catalyst and subsequent acetylation of the resulting free hydroxy groups with acetic anhydride and pyridine can yield compound (1) in which Y is

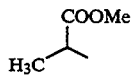

and $R_1$ is Ac.

Compound (9), a trisaccharide intermediate can be prepared from a known compound according to the reaction steps shown in Reaction Scheme 6 below.

The reaction is started from compound (18) which is obtained, for example, by reacting compound 1 described by T. Murase, A. Hasegawa et al. in Carbohydrate Research 188, 71–80, 1989 with an excess amount of DMP in DMF at 50° C. to 100° C. for 5 hours to 8 hours in the presence of an acid catalyst such as PTS. Then, compound (18) is reacted with, e.g., benzoyl chloride in pyridine at −50° C. to give compound (19) containing a free hydroxyl group only at the 3-position of the glucose. For instance, Compound 5 described, by F. Yamazaki, T. Ogawa et al., in Carbohydrate Research, 201, 31–50, 1990 is employed as a sugar donor, Compound (20). Compound (19) is employed as a sugar acceptor. The condensation of the sugar donor and the sugar acceptor is accomplished, e.g., in benzene in the presence of DMTST to afford compound (9).

According to a conventional way, the compounds of formula (I) can be converted to their salts with an alkali metal such as sodium and potassium or an alkaline earth metal such as calcium and magnesium. The salts thus obtained have pharmacological activities similar to those of the compounds of the invention in free form and are included within the scope of the invention.

As demonstrated in Examples 5–8 below, the compounds of the present invention have a function of antagonistically inhibiting an adhesion between ELAM-1 expressed on vascular endothelial cells by stimulus from the inflammatory site and leukocytes, cancer cells or the like. Thus, inflammation-related serious tissue destruction can be avoided by preventing leukocytes from leaving blood flow and damaging the tissues. Inhibiting the adhesion of cancer cells results in inhibiting hematogenous metastasis of cancers. Therefore, the compounds of the present invention are useful as a medicament such as an antiinflammatory agent, a therapeutic

REACTION SCHEME 6

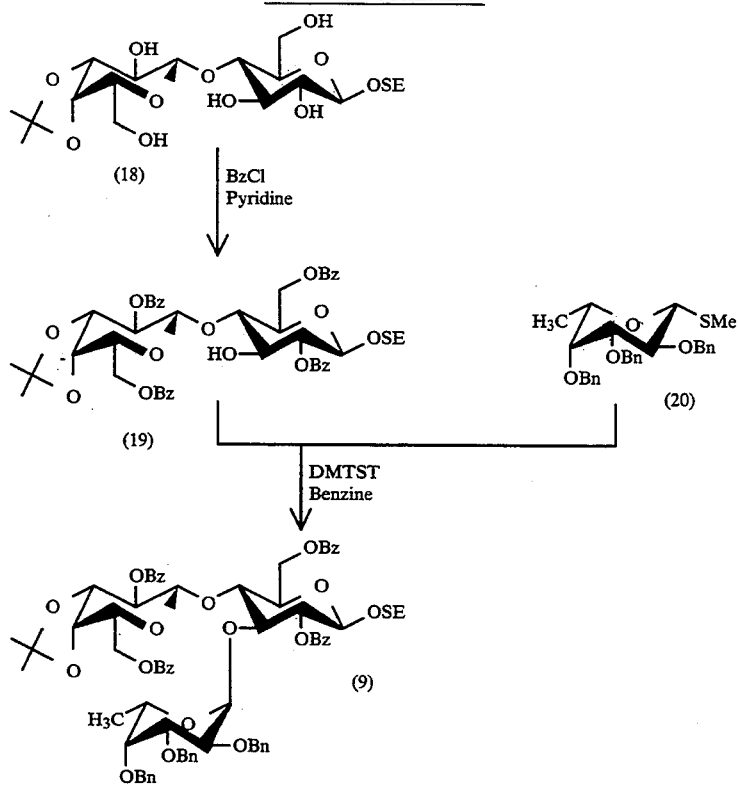

agent for rheumatoid arthritis, and an agent for inhibiting the metastasis of cancers.

Thus, the present invention also provides pharmaceutical compositions comprising a glycolipid derivative of formula (I) or a pharmaceutically acceptable salt thereof and pharmaceutically acceptable carriers.

It is desirable to administer the composition by intravenous injection, but an oral administration is also feasible. Usually, a daily dose of the active ingredient for adult is in the range of 1.2–3600 mg. It is preferable to divide the dose into 4–8 doses per day. The dosage may appropriately be increased or decreased depending upon conditions of the patient such as symptom, age, sex and bodyweight. Of course it is changeable with the route of administration, oral or parenteral.

The pharmaceutical composition may be formulated in any of oral or parenteral forms such as powders, granules, tablets, capsules, injections, oily emulsions and liposomes.

In preparing the formulations conventional additives may be added including excipients, stabilizers, preservatives, solubilizers, wetting agents, emulsifiers, lubricants, sweeteners, colorants, flavors, tonicity modifiers, buffers and antioxidants.

As the formulations preferable for administration in unit dosage form may be used oily emulsions and liposomes. The oily emulsions can be prepared by using a natural fat such as soybean oil as an oil component and an emulsifier such as, soybean lecithin or egg yolk lecithin. In addition to the above-mentioned components, an isotonicity-inducing agent such as, glycerin and an emulsification adjuvant such as a variety of surfactants may be employed. The oily emulsions can be used as injections for intravenous, intramuscular or subcutaneous injection.

Liposomes are formed from a fat capable of forming standard vacuoles. Major fats for forming the liposome include phosphatidylcholine and sphingomyelin, to which is added dicetyl phosphate, phosphatidic acid, phosphatidylserine or the like for stabilization with electric charge. Preparation of the liposomes is carried out by such a technique as ultrasonication, ethanol injection, ether injection or negative-phase evaporation. The liposomes may be encapsulated with a desired drug or enzyme so that it can effectively be transferred to the site of inflammation by utilizing an affinity of the compounds of the invention with ELAM-1.

The invention is further illustrated by the following examples. Reference Examples 1-3 are given to illustrate the synthesis of the starting materials used in the invention. It is noted that the marks A-D attached to the compound number (for example, as in compound (1A )) are used for identifying a specific compound of a group of compounds with a compound number assigned in Reaction Schemes 1-6.

Reference Example 1

Synthesis of compound (9), 2-(trimethylsilyl)ethyl O-(2,6-di-O-benzoyl-β-D-galactopyranosyl)-(1→4)-[O-(2,3,4-tri-O-benzyl-β-L-fucopyranosyl)-(1→3)-2,6-di-O-benzoyl-β-D-glucopyranoside]. (Reaction Scheme 6).

1-1 Synthesis of compound (19)

To a solution of compound (18) (105 mg, 0.218 mmol) in a mixed solvent of methylene chloride:pyridine=4:1 (5 ml) cooled to −50° C. was added BzCl (0.25 ml), and the mixture was stirred for 30 min. After completion of the reaction as confirmed by TLC (methylene chloride:methanol=40:1), the excess reagent was decomposed by addition of methanol followed by concentration under reduced pressure. A syrup thus obtained was extracted with methylene chloride, and the organic layer washed with 1N-HCl and water, dehydrated over $Na_2SO_4$, which was then separated by filtration and the filtrate concentrated under reduced pressure. The resulting syrup was subjected to column chromatography to give compound (19) (140 mg, 71.6%) with an eluent (ethyl acetate:hexane=1:2).

$C_{48}H_{54}O_{15}Si(899.031)$

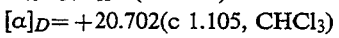

$[\alpha]_D = +20.702(c\ 1.105,\ CHCl_3)$

IR $\nu$ (film, max.) cm$^{-1}$: 3100–2800 (CH); 1730 (ester); 860, 840 (TMS); 710 (phenyl).

$^1$H NMR (300 MHz, CDCl$_3$): 8.26–7.42 (m, 20H, 40 Bz); 5.38 (dd, 1H, $J_{1,2}$=8.08 Hz, $J_{2,3}$=9.56 Hz, H-2); 5.53 (t, 1H, $J_{1',2'}$=$J_{2',3'}$=7.83 Hz, H-2'); 5.03 (dd, 1H, $J_{5,6}$=2.43 Hz, $J_{gem}$=12.40 Hz, H-6); 4.82 (d, 1H, $J_{1',2'}$=8.19 Hz, H-1'); 4.71 (d, 1H, H-1); 4.59 (dd, 1H, $J_{5,6}$=9.85 Hz, H-6); 4.53 (m, 2H, H-3',6'); 4.43 (nd, 1H, $J_{3',4'}$=3.68 Hz, H-4'); 4.36 (dd, 1H, $J_{5',6'}$=4.32 Hz, $J_{gem}$=12.01 Hz, H-6'); 4.15 (t, 1H, $J_{2,3}$=$J_{3,4}$=9.56 Hz, H-3); 4.01 (m, 1H, CHCH$_2$Si); 3.89 (t, 1H, H-4); 3.82 (m, 1H, H-5); 3.64 (m, 1H, CH'CH$_2$Si); 1.80, 1.50 (2 s, 6H, 2 Me); 0.95 (m, 2H, CH$_2$CH$_2$Si); 0.00 (s, 9H, SiMe).

1-2 Synthesis of compound (9)

To a solution of compound (20) (1.20 g, 2.58 mmol) and compound (19) (1.20 g, 1.33 mmol) in benzene (50 ml) was added MS 4A (10 g), and the mixture stirred for 24 hours at room temperature. To the resulting mixture cooled to 5° C. was added DMTST (3.0 g, 70%), and the mixture stirred for 5 hours. After completion of the reaction as confirmed by TLC (methylene chloride:methanol=40:1), the reaction solution was filtered through Celite, and combined filtrate and washings extracted with methylene chloride. The organic layer was washed with $Na_2CO_3$ and $H_2O$, dehydrated over $Na_2SO_4$, which was then separated by filtration, and the filtrate concentrated under reduced pressure. The resulting syrup was subjected to column chromatography to give compound (9) (1.46 g, 83.0%) with an eluent (ethyl acetate:hexane=1:4).

$C_{75}H_{82}O_{19}Si$ (1315.548)

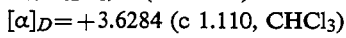

$[\alpha]_D = +3.6284\ (c\ 1.110,\ CHCl_3)$

IR $\nu$ (film, max.) cm$^{-1}$: 3150–2800 (CH); 1720 (ester); 860, 840 (TMS); 710 (phenyl).

$^1$H NMR (300 MHz, CDCl$_3$): Fucose unit: 5.42 (d, 1H, $J_{1,2}$=3.54 Hz, H-1); 4.22 (m, 1H, H-3); 3.91 (dd, 1H, $J_{1,2}$=3.76 Hz, $J_{2,3}$=10.15 Hz, H-2); 1.29 (d, 3H, $J_{5,6}$=6.26 Hz, Me). Lactose unit: 8.18–6.92 (m, 35H, 40 Bz, 30 Bn); 5.40 (dd, 1H, $J_{1,2}$=7.92 Hz, $J_{2,3}$=9.44 Hz, H-2); 5.23 (t, 1H, $J_{1',2'}$=$J_{2',3'}$=7.92 Hz, H-2'); 4.36 (dd, 1H, $J_{5',6'}$=7.21 Hz, $J_{gem}$=10.62 Hz, H-6'); 4.48 (m, 2H, H-3,6); 4.47 (dd, 1H, $J_{3',4'}$=3.65 Hz, H-3'); 4.44 (d, 1H, H-1); 4.23 (d, 1H, H-1'); 4.10 (t, 1H, $J_{3,4}$=$J_{4,5}$=9.50 Hz, H-4); 3.81 (m, 1H, H-5'); 3.77 (m, 1H, CHCH$_2$Si); 3.50 (m, 1H, H-5); 3.34 (m, 1H, CH'CH$_2$Si); 1.58, 1.49 (2s, 6H, 2 Me); 0.72 (m, 2H, CH$_2$CH$_2$Si); 0.00 (s, 9H, SiMe).

Reference Example 2

Synthesis of compound (1A), 2-(trimethylsilyl)ethyl O-(methyl 5-acetamido-4,7,8,9-tetra-O-acetyl-3,5-dideoxy-D-glycero-α-D-galacto-2-nonulopyranosylonate)-(2→3)-O-(4-O-acetyl-2,6-di-O-benzoyl-β-D-galactopyranosyl)-(1→4)-[O-(2,3,4-tri-O-acetyl-α-L-fucopyranosyl)-(1→3)-2,6-di-O-benzoyl-β-D-glucopyranoside] (Reaction Scheme 3).

2-1 Synthesis of compound (10)

A solution of compound (9) (1.58 g, 1.20 mmol) in 80% acetic acid (50 ml) was stirred at 50° C. for 3 days. After completion of the reaction as confirmed by TLC (methylene chloride:methanol=40:1), the reaction solution was concentrated under reduced pressure. The resulting syrup was subjected to column chromatography to give compound (10) (1.21 g, 79.1%) with an eluent (ethyl acetate:hexane=1:2).

$C_{72}H_{78}O_{19}Si$ (1275.483)

$[\alpha]_D = -14.241$ (c 0.990, CHCl$_3$)

IR $\nu$ (film, max.) cm$^{-1}$: 3700–3300 (OH); 3150–2850 (CH); 1730 (ester); 860, 840 (TMS); 710 (phenyl).

$^1$H NMR (300 MHz, CDCl$_3$): Fucose unit: 5.57 (d, 1H, $J_{1,2}$=3.69 Hz, H-1); 4.07 (dd, 1H, $J_{2,3}$=10.28 Hz, H-2); 1.49 (d, 3H, $J_{5,6}$=6.42 Hz, Me). Lactose unit: 8.28–7.16 (m, 35H, 40 Bz, 30 Bn); 5.61 (dd, 1H, $J_{1,2}$=7.85 Hz, $J_{2,3}$=9.59 Hz, H-2); 5.43 (dd, 1H, $J_{1',2'}$=8.23 Hz, $J_{2',3'}$=9.56 Hz, H-2'); 4.75 (d, 1H, H-1'); 4.62 (d, 1H, H-1); 4.39 (t, 1H, $J_{2,3}$=$J_{3',4'}$=10.17 Hz, H-3); 3.80 (dd, 1H, $J_{3',4'}$=2.93 Hz, H-3'); 3.96 (m, 1H, CHCH$_2$Si); 3.59 (m, 1H, CH'CH$_2$Si); 0.92 (m, 2H, CH$_2$CH$_2$Si); 0.00 (s, 9H, SiMe).

2-2 Synthesis of compound (12)

To a solution of compound (11) (1.02 g, 1.97 mmol) and compound (10) (1.20 g, 0.94 mmol) in acetonitrile (25 ml) was added MS 3A (15 g), and the mixture stirred for 24 hours at room temperature. To the resulting mixture cooled to −45° C. were added NIS (1.2 g) and TfOH (120 ml), and the mixture stirred for 24 hours. After completion of the reaction as confirmed by TLC (methylene chloride:methanol=40:1), the reaction solution was filtered through Celite, and combined filtrate and washings extracted with methylene chloride. The organic layer was washed with Na$_2$CO$_3$ and H$_2$O, dehydrated over Na$_2$SO$_4$, which was then separated by filtration, and the filtrate concentrated under reduced pressure. The resulting syrup was subjected to column chromatography to give compound (12) (0.90 g, 54.5%) with an eluent (methylene chloride:methanol=40:1). $C_{92}H_{105}O_{31}Si$ (1748.914)

2-3 Synthesis of compound (1A)

To a vessel in which a palladium/carbon catalyst (900 mg) had been dispersed in a mixed solvent of ethanol:acetic acid=6:1 (70 ml), was added a solution of compound (12) (890 mg, 0.51 mmol) in ethanol (5 ml), and the mixture stirred for 24 hours under an atmosphere of hydrogen. After completion of the reaction as confirmed by TLC (methylene chloride:methanol=40:1), the reaction solution was filtered through Celite, and combined filtrate and washings concentrated under reduced pressure to dryness. The resulting syrup was dissolved in pyridine (30 ml) followed by addition of acetic anhydride (20 ml), and the mixture was stirred daylong at room temperature. After completion of the reaction as confirmed by TLC (methylene chloride:methanol=30:1), methanol was added to destroy the excess reagent followed by concentration under reduced pressure. The resulting syrup was extracted with methylene chloride, and the organic layer washed with 1N-HCl and H$_2$O, dehydrated over Na$_2$SO$_4$, which was then separated by filtration, and the filtrate concentrated under reduced pressure. The resulting syrup was subjected to column chromatography to give compound (1A) (718 mg, 85.7%) with an eluent (methylene chloride:methanol=30:1).

$C_{79}H_{95}O_{35}Si$ (1646.678)

$[\alpha]_D = -1.8534$ (c 0.985, CDCl$_3$)

IR $\nu$ (film, max.) cm$^{-1}$: 3700–3150 (NH); 3150–2800 (CH); 1750 (ester); 1670, 1540 (amide); 860, 840 (TMS); 710 (phenyl).

$^1$H NMR (300 MHz, CDCl$_3$): Fucose unit: 5.44 (d, 1H, $J_{1,2}$=2.61 Hz, H-1); 5.30 (m, 2H, H-2,5); 1.33 (d, 3H, $J_{5,6}$=6.55 Hz, Me). Lactose unit: 5.33 (dd 1H, $J_{1,2}$=7.97 Hz, $J_{2,3}$=9.34 Hz, H-2); 5.30 (dd, 1H, $J_{1',2'}$=7.971 Hz, H-2'); 5.10 (d, 1H, H-1'); 5.05 (d, 1H, $J_{3',4'}$=2.92 Hz, H-4'); 4.74 (dd, 1H, $J_{2',3'}$=10.08 Hz, H-3'); 4.69 (m, 2H, H-6'); 4.45 (dd, 1H, $J_{5,6}$=3.72 Hz, $J_{gem}$=12.27 Hz, H-6); 4.40 (d, 1H, H-1); 4.21 (dd, 1H, $J_{5,6}$=3.43 Hz, H-6); 4.13 (t, 1H, $J_{2,3}$=$J_{3,4}$=9.34 Hz, H-3); 3.94 (m, 1H, H-5'); 3.80 (m, 1H, CHCH$_2$Si); 3.46 (m, 1H, H-5); 3.36 (m, 1H, CH'CH$_2$Si); 0.72 (m, 2H, CH$_2$CH$_2$Si); 0.00 (s, 9H, SiMe). Sialic acid unit: 5.64 (m, 1H, H-8); 5.27 (dd, 1H, $J_{6,7}$=2.95 Hz, $J_{7,8}$=6.94 Hz, H-7); 4.89 (d, 1H, $J_{5,NH}$=10.27 Hz, NH); 4.83 (m, 1H, H-4); 4.37 (dd, 1H, $J_{8,9}$=2.21 Hz, $J_{gem}$=10.61 Hz, H-9); 4.22 (dd, 1H, H-9'); 3.77 (s, 1H, COOMe); 3.74 (m, 1H, H-5); 3.50 (dd, 1H, $J_{5,6}$=10.65 Hz, H-6); 2.52 (dd, 1H, $J_{gem}$=12.48 Hz, $J_{3e,4}$=4.57 Hz, H-3e); 1.74 (t, 1H, H-3a). Other unit: 8.23–7.25 (m, 20H, 40 Bz); 2.20, 2.11, 2.06, 1.94, 1.88, 1.87, 1.76, 1.67, 1.43 (9 s, 27H, 80 Ac, NAc).

Reference Example 3

Synthesis of compound (3) (Reaction Scheme 2)

3-1 Synthesis of compound (3A), 1-para-(2-tetradecylhexadecanoyl)aminobenzyl-3-oxapentane-1,5-diol

3-3-1 Synthesis of compound (7A)

To a solution of diethylene glycol (500 mg, 4.71 mmol) in benzene (5 ml) cooled to 10° C. were added silver oxide (3.3 g) and para-nitrobenzyl bromide (1.0 g), and the mixture stirred under light shield for 8 hours. After completion of the reaction as confirmed by TLC (methylene chloride:methanol=20:1), methanol was added to destroy the excess reagent. The resulting mixture was filtered through Celite, and combined filtrate and washings concentrated under reduced pressure. The resulting syrup was subjected to column chromatography to give compound (7A) (730 mg, 64.2%) with an eluent (methylene chloride:methanol=25:1).

$C_{11}H_{15}NO_5$ (241.244)

IR $\nu$ (film, max.) cm$^{-1}$: 3700–3150 (OH); 3150–2700 (CH); 1520, 1350 (NO$_2$); 740 (phenyl).

$^1$H NMR (300 MHz, CDCl$_3$): 8.19–7.55 (m, 4H, phenyl); 4.69 (s, 2H, CH$_2$Ph); 3.73–3.63 (m, 8H, OCH$_2$CH$_2$O); 3.18 (broad, 1H, OH).

3-1-2 Synthesis of compound (3A)

To a vessel in which a palladium/carbon catalyst (50 mg) had been dispersed in ethanol (10 ml), was added a solution of compound (7A) (108 mg, 0.448 mmol) in ethanol (5 ml). The mixture was stirred under an atmosphere of hydrogen for 30 min. After completion of the reaction as confirmed by TLC (methylene chloride:methanol=20:1), the reaction solution was filtered through Celite, and combined filtrate and washings concentrated under reduced pressure to dryness. The resulting syrup was dissolved in methylene chloride (5 ml). To the solution were added WSC (200 mg) and 2-tetradecylhexadecanoic acid (470 mg), and the mixture stirred at room temperature for 2 hours. After completion of the reaction as confirmed by TLC (methylene chloride:methanol=30:1), the reaction mixture was concentrated under reduced pressure. The resulting syrup was subjected to column chromatography to give compound (3A) (220 mg, 76.1%) with an eluent (methylene chloride:methanol=30:1).

$C_{41}H_{75}NO_4$ (646.055)

IR $\nu$ (film, max.) cm$^{-1}$: 3650–3100 (OH); 3100–2700 (CH); 1650, 1530 (amide); 720 (phenyl).

$^1$H NMR (300 MHz, CDCl$_3$): 7.87–7.23 (m, 5H, HN phenyl); 4.50 (s, 2H, CH$_2$Ph); 3.72–3.57 (m, 20H, OCH$_2$CH$_2$O); 2.95 (broad, 1H, OH); 2.20 (m, 1H, H-2); 1.72–1.40 (m, 4H, H-3,3'); 1.24 (s, 48H, CH$_2$); 0.88 (t, 6H, CH$_3$).

3-2 Synthesis of compound (3B), 1-para-(2-tetradecylhexadecanoyl)aminobenzyl-3,6-dioxaoctane-1,8-diol

3-2-1 Synthesis of compound (7B)

To a solution of triethylene glycol (500 mg, 3.33 mmol) in benzene (5 ml) cooled to 10° C. were added silver oxide (1.30 g) and para-nitrobenzyl bromide (410 mg), and the mixture stirred under light shield for 5 hours. After completion of the reaction as confirmed by TLC (methylene chloride:methanol=30:1), methanol was added to destroy the excess reagent. The resulting mixture was filtered through Celite, and combined filtrate and washings concentrated under reduced pressure. The resulting syrup was subjected to column chromatography to give compound (7B) (485 mg, 51.1%) with an eluent (methylene chloride:methanol=30:1).

$C_{13}H_{19}NO_6$ (285.296)

IR $\nu$ (film, max) cm$^{-1}$: 3700–3150 (OH); 3150–2700 (CH); 1520, 1350 (NO$_2$); 740 (phenyl).

$^1$H NMR (300 MHz, CDCl$_3$): 8.20–7.52 (m, 4H, phenyl); 4.68 (s, 2H, CH$_2$Ph); 3.75–3.60 (m, 12H, OCH$_2$CH$_2$O); 3.12 (broad, 1H, OH).

3-2-2 Synthesis of compound (3B)

To a vessel in which a palladium/carbon catalyst (50 mg) had been dispersed in ethanol (10 ml), was added a solution of compound (7B) (105 mg, 0.368 mmol) in ethanol (5 ml). The mixture was stirred under an atmosphere of (hydrogen for 1 hour. After completion of the reaction as confirmed by TLC (methylene chloride:methanol=20:1), the reaction solution was filtered through Celite, and combined filtrate and washings concentrated under reduced pressure to dryness. The resulting syrup was dissolved in methylene chloride (5 ml). To the solution were added WSC (200 mg) and 2-tetradecylhexadecanoic acid (400 mg), and the mixture stirred at room temperature for 2 hours. After completion of the reaction as confirmed by TLC (methylene chloride:methanol=30:1), the reaction mixture was concentrated under reduced pressure. The resulting syrup was subjected to column chromatography to give compound (3B) (170 mg, 66.9%) with an eluent (methylene chloride:methanol=30:1).

$C_{43}H_{79}NO_5$ (690.108)

IR $\nu$ (film, max.) cm$^{-1}$: 3650–3100 (OH); 3100–2700 (CH); 1650, 1530 (amide); 720 (phenyl).

$^1$H NMR (300 MHz, CDCl$_3$): 7.61–7.26 (m, 5H, HN phenyl); 4.51 (s, 2H, CH$_2$Ph); 3.73–3.59 (m, 12H, OCH$_2$CH$_2$O); 2.75 (broad, 1H, OH); 2.18 (m, 1H, H-2); 1.71–1.41 (m, 4H, H-3,3'); 1.24 (s, 48H, CH$_2$); 0.88 (t, 6H, CH$_3$).

3-3 Synthesis of compound (3C), 1-para-(2-tetradecylhexadecanoyl)aminobenzyl-3,6,9-trioxaundecane-1,11-diol

3-3-1 Synthesis of compound (7C)

To a solution of tetraethylene glycol (500 mg, 2.57 mmol) in benzene (5 ml) cooled to 10° C. were added silver oxide (1.80 g) and para-nitrobenzyl bromide (560 mg), and the mixture stirred under light shield for 3 days. After completion of the reaction as confirmed by TLC (methylene chloride:methanol=30:1), methanol was added to destroy the excess reagent. The resulting mixture was filtered through Celite, and combined filtrate and washings concentrated under reduced pressure. The resulting syrup was subjected to column chromatography to give compound (7C) (480 mg, 56.6%) with an eluent (methylene chloride:methanol=30:1).

$C_{15}H_{23}NO_7$ (329.350)

IR $\nu$ (film, max.) cm$^{-1}$: 3700–3150 (OH); 3150–2700 (CH); 1520, 1350 (NO$_2$); 740 (phenyl).

$^1$H NMR (300 MHz, CDCl$_3$): 8.21–7.52 (m, 4H, phenyl); 4.68 (s, 2H, CH$_2$Ph); 3.72–3.60 (m, 16H, OCH$_2$CH$_2$O); 2.99 (broad, 1H, OH).

3-3-2 Synthesis of compound (3C)

To a vessel in which a palladium/carbon catalyst (50 mg) had been dispersed in ethanol (10 ml), was added a solution of compound (7C) (98 mg, 0.298 mmol) in ethanol (5 ml). The mixture was stirred under an atmosphere of hydrogen for 50 min. After completion of the reaction as confirmed by TLC (methylene chloride:methanol=20:1), the reaction mixture was filtered through Celite, and combined filtrate and washings concentrated under reduced pressure to dryness. The re-suiting syrup was dissolved in methylene chloride (5 ml). To the solution were added WSC (200 mg) and 2-tetradecylhexadecanoic acid (350 mg), and the mixture stirred at room temperature for 4 hours. After completion of the reaction as confirmed by TLC (methylene chloride:methanol=30:1), the reaction mixture was concentrated under reduced pressure. The resulting syrup was subjected to column chromatography to give compound (3C) (132 mg, 60.6%) with an eluent (methylene chloride:methanol=30:1).

$C_{45}H_{83}NO_6$ (734.161)

IR $\nu$ (film, max.) cm$^{-1}$: 3650–3100 (OH); 3100–2750 (CH); 1650, 1530 (amide); 720 (phenyl).

$^1$H NMR (300 MHz, CDCl$_3$): 7.54–7.27 (m, 5H, HN phenyl); 4.51 (s, 2H, CH$_2$Ph); 3.72–3.58 (m, 16H, OCH$_2$CH$_2$O); 2.83 (broad, 1H, OH); 2.16 (m, 1H, H-2); 1.71–1.44 (m, 4H, H-3,3'); 1.24 (s, 48H, CH$_2$); 0.88 (t, 6H, CH$_3$).

3-4 Synthesis of compound (3D), 1-para-(2-tetradecylhexadecanoyl)aminobenzyl-3,6,9,12-tetraoxatetradecane-1,14-diol

3-4-1 Synthesis of compound (7D)

To a solution of heptaethylene glycol (500 mg, 2.10 mmol) in benzene (5 ml) cooled to 10° C. were added silver oxide (1.46 g) and para-nitrobenzyl bromide (460 mg), and the mixture stirred under light shield for one day. After completion of the reaction as confirmed by TLC (methylene chloride:methanol=30:1), methanol was added to destroy the excess reagent. The resulting mixture was filtered through Celite, and combined filtrate and washings concentrated under reduced pressure. The resulting syrup was subjected to column chromatography to give compound (7D) (536 mg, 68.4%) with an eluent (methylene chloride:methanol=30:1).

$C_{17}H_{27}NO_8$ (373.403)

IR $\nu$ (film, max.) cm$^{-1}$: 3700–3150 (OH); 3150–2700 (CH); 1520, 1350 (NO$_2$); 740 (phenyl).

$^1$H NMR (300 MHz, CDCl$_3$): 8.20–7.52 (m, 4H, phenyl); 4.69 (s, 2H, CH$_2$Ph); 3.72–3.59 (m, 20H, OCH$_2$CH$_2$O); 3.06 (broad, 1H, OH).

3-4-2 Synthesis of compound (3D)

To a vessel in which a palladium/carbon catalyst (50 mg) had been dispersed in ethanol (10 ml) was added a solution of compound (7D) (120 mg, 0.321 mmol) in ethanol (5 ml). The mixture was stirred under an atmosphere of hydrogen for 35 min. After completion of the reaction as confirmed by TLC (methylene chloride:methanol=20:1), the reaction solution was filtered through Celite, and combined filtrate and washings concentrated under reduced pressure to dryness. The resulting syrup was dissolved in methylene chloride (5 ml). To the solution were added WSC (200 mg) and 2-tetradecylhexadecanoic acid (370 mg), and the mixture stirred at room temperature for 2 hours. After completion of the reaction as confirmed by TLC (methylene chloride:methanol=30:1), the reaction mixture was concentrated under reduced pressure. The resulting syrup was subjected to column chromatography to give compound (3D) (194 mg, 77.6%) with an eluent (methylene chloride:methanol=30:1).

$C_{47}H_{87}NO_7$ (778.214)

IR $\nu$ (film, max.) cm$^{-1}$: 3700–3150 (OH); 3150–2700 (CH); 1650, 1530 (amide); 720 (phenyl).

$^1$H NMR (300 MHz, CDCl$_3$): 7.80–7.28 (m, 5H, HN phenyl); 4.50 (s, 2H, CH$_2$Ph); 3.71–3.58 (m, 20H, OCH$_2$CH$_2$O); 3.02 (broad, 1H, OH); 2.19 (m, 1H, H-2); 1.69–1.41 (m, 4H, H-3,3'); 1.24 (s, 48H, CH$_2$); 0.88 (t, 6H, CH$_3$).

EXAMPLE 1

Synthesis of compound (5A),
O-(5-acetamido-3,5-dideoxy-D-glycero-α-D-galacto-2-nonulopyranosylonic acid)-(2→3)-O-β-D-galactopyranosyl-(1→4)-[O-α-L-fucopyranosyl-(1→3)-O-β-D-glucopyranosyl]-(1→1)-5-O-para-(2-tetradecylhexadecanoyl)-aminobenzyl-3-oxapentane-1,5-diol (Reaction Scheme 1)

1-1 Synthesis of compound (2A),
O-(methyl-5-acetamido-4,7,8,9-tetra-O-acetyl-3,5-dideoxy-D-glycero-α-D-galacto-2-nonulopyranosylonate)-(2→3)-O-(4-O-acetyl-2,6-di-O-benzoyl-β-D-galactopyranosyl)-(1→4)-[O-(2,3,4-tri-O-acetyl-α-L-fucopyranosyl)-(1→3)-O-(2,6-di-O-benzoyl-α-D-glucopyranosyl)]trichloroacetimidate To an ice-cooled solution of compound (1A) (106 mg, 0.064 mmol) in methylene chloride (3.0 ml) was added dropwise trifluoroacetic acid (6.0 ml), and the mixture stirred at 0° C. for 1 hour. After completion of the reaction as confirmed by TLC (methylene chloride:methanol=25:1), ethyl acetate was added to destroy the excess reagent, and the mixture concentrated under reduced pressure. To a solution of the concentrate in methylene chloride (2 ml) were added DBU (10 mg) and trichloroacetonitrile (2.0 ml) under ice-cooling, and the mixture stirred at 0° C. for 2.5 hours. After completion of the reaction as confirmed by TLC (methylene chloride:methanol=30:1), the mixture was concentrated under reduced pressure. The resulting syrup was subjected to column chromatography to give compound (2A) (92 mg, 85.0%) with an eluent (methylene chloride:methanol=30:1).

$C_{76}H_{83}N_2O_{35}Cl_3$ (1690.838)

$[\alpha]_D = +0.195$ (c 1.025, CHCl$_3$)

IR $\nu$ (film, max.) cm$^{-1}$: 3700–3150 (NH); 3150–2850 (CH); 1740 (ester); 1680, 1540 (amide); 710 (phenyl).

$^1$H NMR (300 MHz, CDCl$_3$): Fucose unit: 5.40 (d, 1H, $J_{1,2}=3.79$ Hz, H-1); 5.28 (m, 2H, H-2,5); 1.39 (d, 3H, $J_{5,6}=6.51$ Hz, Me). Lactose unit: 6.47 (d, 1H, $J_{1,2}=3.70$ Hz, H-1); 5.41 (dd, 1H, $J_{2,3}=9.52$ Hz, H-2); 5.32 (dd, 1H, $J_{1',2'}=8.08$ Hz, $J_{2',3'}=10.01$ Hz, H-2'); 5.12 (d, 1H, $J_{1',2'}=7.69$ Hz, H-1'); 5.11 (d, 1H, $J_{3',4'}=3.27$ Hz, H-4'); 4.87–4.78 (m, 2H, H-3',6); 4.74 (dd, 1H, $J_{5',6'}=7.89$ Hz, $J_{gem}=11.46$ Hz, H-6'); 4.62 (dd, 1H, $J_{5',6'}=6.26$ Hz, H-6'); 4.49 (dd, 1H, $J_{5,6}=4.33$ Hz, $J_{gem}=12.53$ Hz, H-6); 4.39 (t, 1H, $J_{2,3}=J_{3,4}=9.51$ Hz, H-3); 3.98 (m, 1H, H-5'); 3.75 (m, 1H, H-5). Sialic acid unit: 5.65 (m, 1H, H-8); 5.25 (dd, 1H, $J_{6,7}=2.92$ Hz, $J_{7,8}=10.49$ Hz, H-7); 4.83 (m, 1H, H-4); 4.37 (dd, 1H, $J_{gem}=12.82$ Hz, H-9); 4.17 (dd, 1H, H-9'); 3.75 (s, 1H, COOMe); 3.74 (m, 1H, H-5); 3.53 (dd, 1H, $J_{5,6}=10.69$ Hz, H-6); 2.54 (dd, 1H, $J_{gem}=12.32$ Hz, $J_{3e,4}=4.27$ Hz, H-3e); 1.67 (t, 1H, H-3a). Other unit: 8.49 (s, 1H, C=NH); 8.19–7.31 (m, 20H, 40 Bz); 2.21, 2.14, 2.02, 1.94, 1.88, 1.75, 1.69, 1.67, 1.45 (9 s, 27H, 8O Ac, NAc).

1-2 Synthesis of compound (4A),
O-(methyl-5-acetamido-4,7,8,9-tetra-O-acetyl-3,5-dideoxy-D-glycero-α-D-galacto-2-nonulopyranosylonate)-(2→3)-O-(4-O-acetyl-2,6-di-O-benzoyl-β-D-galactopyranosyl)-(1→4)-[3-O-(2,3,4-tri-O-acetyl-α-L-fucopyranosyl)-(1→3)-O-(2,6-di-O-benzoyl-β-D-glucopyranosyl)]-(1→1)-5-O-para-(2-tetradecylhexa-decanoyl)aminobenzyl-3-oxapentane-1,5-diol To a solution of compound (2A) (110 mg, 0.0651 mmol) and compound (3A) (85 mg, 0.132 mmol) in methylene chloride (3 ml) was added MS 4A AW300 (2 g), and the mixture stirred at room temperature for 1 hour. To the resulting mixture cooled with ice, was added BF$_3$.OEt$_2$ (0.05 ml) and stirred for 5 hours. After completion of the reaction as confirmed by TLC (methylene chloride:methanol=30:1), the reaction solution was filtered through Celite, and combined filtrate and washings extracted with methylene chloride. The organic layer was washed with Na$_2$CO$_3$ and H$_2$O, dehydrated over Na$_2$SO$_4$, which was then separated by filtration, and the filtrate was concentrated under reduced pressure. The resulting syrup was subjected to column chromatography to give compound (4A) (105 mg, 74.5%) with an eluent (methylene chloride:methanol=33:1).

$C_{115}H_{156}N_2O_{38}$ (2174.489)

$[\alpha]_D = -1.8310$ (c 1.125, CHCl$_3$)

IR $\nu$ (film, max.) cm$^{-1}$: 3400–3200 (NH); 3200–2800 (CH); 1750 (ester); 1660, 1530 (amide); 710 (phenyl).

$^1$H NMR (300 MHz, CDCl$_3$): Fucose unit: 5.45 (d, 1H, $J_{1,2}=2.38$ Hz, H-1); 5.28 (m, 2H, H-2,5); 5.03 (dd, 1H, $J_{2,3}=10.71$ Hz, $J_{3,4}=3.78$ Hz, H-3); 1.34 (d, 3H, $J_{5,6}=6.48$ Hz, Me). Lactose unit: 5.33 (dd, 1H, $J_{1,2}=8.03$ Hz, $J_{2,3}=9.37$ Hz, H-2); 5.30 (dd, 1H, $J_{1',2'}=8.12$ Hz, $J_{2',3'}=10.21$ Hz, H-2'); 5.12 (d, 1H, H-1'); 5.06 (d, 1H, $J_{3',4'}=3.50$ Hz, H-4'); 4.76 (dd, 1H, H-3'); 4.69 (m, 2H, H-6'); 4.52 (d, 1H, H-1); 4.46 (dd, 1H, $J_{5,6}=3.16$ Hz, $J_{gem}=12.50$ Hz, H-6); 4.27 (dd, 1H, $J_{5,6}=8.47$ Hz, H-6); 4.12 (t, 1H, $J_{2,3}=J_{3,4}=9.37$ Hz, H-3); 3.95 (m, 1H, H-5'); 3.38 (m, 1H, H-5). Sialic acid unit: 5.64 (m, 1H, H-8); 5.26 (dd, 1H, $J_{6,7}=2.72$ Hz, $J_{7,8}=6.97$ Hz, H-7); 4.83 (m, 1H, H-4); 4.38 (dd, 1H, $J_{8,9}=1.55$ Hz, $J_{gem}=13.29$ Hz, H-9); 4.22 (dd, 1H, $J_{8,9'}=3.27$ Hz, H-9'); 3.76 (s, 1H, COOMe); 3.75 (m, 1H, H-5); 3.51 (dd, 1H, $J_{5,6}=10.78$ Hz, H-6); 2.52 (dd, 1H, $J_{gem}=12.43$ Hz, $J_{3e,4}=4.38$ Hz, H-3e); 1.66 (t, 1H, H-3a). Other unit: 8.22–7.16 (m, 25H, 40 Bz, NHBn); 3.47–3.18 (m, 8H, OCH$_2$CH$_2$O); 2.20, 2.11, 2.05, 1.94, 1.88, 1.87, 1.75, 1.65, 1.44 (9 s, 27H, 80 Ac, NAc); 1.25 (s, 52H, CH$_2$); 0.88 (t, 6H, CH$_3$).

1-3 Synthesis of compound (5A),
O-(5-acetamido-3,5-dideoxy-D-glycero-α-D-galacto-2-nonulopyranosylonic
acid)-(2→3)-O-β-D-galactopyranosyl-(1→4)-[O-α-L-fucopyranosyl-(1→3)-O-β-D-glucopyranosyl]-(1→1)-5-O-para-(2-tetradecylhexadecanoyl)aminobenzyl-3-oxapentane-1,5-diol To a solution of compound (4A) (103 mg, 0.0474 mmol) in methanol (5 ml) was added 28% sodium methoxide (20 drops), and the mixture stirred for 24 hours at 40° C. Then water (0.5 ml) was added and the resulting mixture stirred overnight. After completion of the reaction as confirmed by TLC (butanol:methanol:water=3:2:1), the reaction mixture was neutralized with ion exchange resin IR-120 (H+), which was then separated by filtration, and the filtrate was concentrated under reduced pressure. The resulting syrup was subjected to gel filtration with Cephadex LH-20 to give compound (5A) (60.6 mg, 90.9%).

$C_{70}H_{122}N_2O_{26}$ (1407.734)

$[\alpha]_D = -30.950$ (c 1.010, chloroform:methanol:water=5:4:0.5)

IR ν (KBr, max.) cm$^{-1}$: 3700–2650 (NH, OH); 2920, 2850 (Me, methylene); 1720 (C=O); 1660, 1540 (amide).

$^1$H NMR (300 MHz, DMSO-D$_2$O): Fucose unit: 5.15 (d, 1H, $J_{1,2}=3.40$ Hz, H-1); 4.58 (m, 1H, H-5); 0.98 (d, 3H, $J_{5,6}=6.28$ Hz, Me). Lactose unit: 4.24 (m, 2H, H-1,1'). Sialic acid unit: 2.73 (broad, 1H, H-3e); 2.30 (nt, 1H, H-3a); 1.87 (s, 3H, NAc). Other unit: 7.53–7.16 (m, 4H, NBn); 4.37 (s, 2H, CH$_2$Ph); 3.26–3.14 (m, 8H, OCH$_2$CH$_2$O); 1.18 (s, 52H, CH$_2$); 0.80 (t, 6H, CH$_3$).

EXAMPLE 2

Synthesis of compound (5B),
O-(5-acetamido-3,5-dideoxy-D-glycero-α-D-galacto-2-nonulopyranosylonic
acid)-(2→3)-O-β-D-galactopyranosyl-(1→4)-[O-α-L-fucopyranosyl-(1→3)-O-β-D-glucopyranosyl]-(1→1)-8-O-para-(2-tetradecylhexadecanoyl)aminobenzyl-3,6-dioxaoctane-1,8-diol (Reaction Scheme 1)

2-1 Synthesis of compound (4B),
O-(methyl-5-acetamido-4,7,8,9-tetra-O-acetyl-3,5-dideoxy-D-glycero-α-D-galacto-2-nonulopyranosylonate)-(2→3)-O-(4-O-acetyl-2,6-di-O-benzoyl-β-D-galactopyranosyl)-(1→4)-[O-(2,3,4-tri-O-acetyl-α-L-fucopyranosyl)-(1→3)-O-2,6-di-O-benzoyl-β-D-glucopyranosyl]-(1→1)-8-O-para-(2-tetradecylhexadecanoyl)aminobenzyl-3,6-dioxaoctane-1,8-diol To a solution of compound (2A) (90 mg, 0.053 mmol) and compound (3β) (73 mg, 0.106 mmol) in methylene chloride (3 ml) was added MS 4A AW300 (2 g), and the mixture stirred at room temperature for 40 min. To the resulting mixture cooled with ice, was added BF$_3$.OEt$_2$ (0.04 ml) and stirred for 3 hours. After completion of the reaction as confirmed by TLC (methylene chloride:methanol=30:1), the reaction mixture was filtered through Celite, and combined filtrate and washings extracted with methylene chloride. The organic layer was washed with Na$_2$CO$_3$ and H$_2$O, dehydrated over Na$_2$SO$_4$, which was then separated by filtration, and the filtrate was concentrated under reduced pressure. The resulting syrup was subjected to column chromatography to give compound (4B) (73 mg, 61.9%) with an eluent (methylene chloride:methanol=30:1).

$C_{117}H_{160}N_2O_{39}$ (2218.542)

$[\alpha]_D = -0.0704$ (c 1.494, CHCl$_3$)

IR ν (film, max.) cm$^{-1}$: 3400–3150 (NH); 3150–2700 (CH); 1750 (ester); 1660, 1530 (amide); 710 (phenyl).

$^1$H NMR (300 MHz, CDCl$_3$): Fucose unit: 5.45 (d, 1H, $J_{1,2}=2.69$ Hz, H-1); 5.26 (m, 2H, H-2,5); 1.34 (d, 3H, $J_{5,6}=6.57$ Hz, Me). Lactose unit: 5.33 (dd, 1H, $J_{1,2}=8.14$ Hz, $J_{2,3}=9.37$ Hz, H-2); 5.30 (dd, 1H, $J_{1',2'}=8.21$ Hz, $J_{2',3'}=10.26$ Hz, H-2'); 5.12 (d, 1H, H-1'); 5.06 (d, 1H, $J_{3',4'}=2.76$ Hz, H-4'); 4.74 (dd, 1H, H-3'); 4.69 (m, 2H, H-6'); 4.49 (m, 1H, H-1); 4.48 (m, 1H, H-6); 4.27 (m, 1H, H-6); 4.12 (t, 1H, $J_{2,3}=J_{3,4}=9.37$ Hz, H-3); 3.93 (m, 1H, H-5'). Sialic acid unit: 5.63 (m, 1H, H-8); 5.25 (dd, 1H, $J_{6,7}=2.77$ Hz, $J_{7,8}=9.74$ Hz, H-7); 4.84 (m, 1H, H-4); 4.38 (dd, 1H, $J_{8,9}=1.95$ Hz, $J_{gem}=11.12$ Hz, H-9); 4.19 (dd, 1H, $J_{8,9'}=3.46$ Hz, H-9'); 3.76 (s, 1H, COOMe); 3.74 (m, 1H, H-5); 3.50 (dd, 1H, $J_{5,6}=11.10$ Hz, H-6); 2.52 (dd, 1H, $J_{gem}=12.40$ Hz, $J_{3e,4}=4.53$ Hz, H-3e); 1.68 (t, 1H, H-3a). Other unit: 8.22–7.23 (m, 25H, 40 Bz, NHBn); 4.34 (s, 2H, CH$_2$Ph); 3.48–3.22 (m, 12H, OCH$_2$CH$_2$O); 2.20, 2.11, 2.05, 1.94, 1.88, 1.87, 1.75, 1.64, 1.43 (9 s, 27H, 80 Ac, NAc); 1.24 (s, 52H, CH$_2$); 0.88 (t, 6H, CH$_3$).

2-2 Synthesis of compound (5B),
O-(5-acetamido-3,5-dideoxy-D-glycero-α-D-galacto-2-nonulopyranosylonic
acid)-(2→3)-O-β-D-galactopyranosyl-(1→4)-[O-α-L-fucopyranosyl-(1→3)-O-β-D-glucopyranosyl]-(1→1)-8-O-para-(2-tetradecylhexadecanoyl)aminobenzyl-3,6-dioxaoctane-1,8-diol To a solution of compound (4B) (72 mg, 0.0325 mmol) in methanol (5 ml) was added 28% sodium methoxide (10 drops), and the mixture stirred at room temperature for 10 hours. Then water (0.5 ml) was added and the mixture stirred for 6 hours. After completion of the reaction as confirmed by TLC (butanol:methanol:water=3:2:1), the reaction mixture was neutralized with ion exchange resin IR-120 (H+), which was then separated by filtration, and the filtrate was concentrated under reduced pressure. The resulting syrup was subjected to gel filtration with Sephadex LH-20 to give compound (5B) (45.5 mg, 96.6%).

$C_{72}H_{126}N_2O_{27}$ (1451.787)

$[\alpha]_D = +58.278$ (c 1.040, chloroform:methanol:water=5:4:0.5)

IR $\nu$ (KBr, max.) $cm^{-1}$: 3700–2650 (NH, OH); 2920, 2850 (Me, methylene); 1720 (C=O); 1660, 1520 (amide).

$^1$H NMR (300 MHz, DMSO-D$_2$O): Fucose unit: 5.18 (d, 1H, $J_{1,2}=3.50$ Hz, H-1); 4.62 (m, 1H, H-5); 1.01 (d, 3H, $J_{5,6}=6.29$ Hz, Me). Lactose unit: 4.28 (m, 2H, H-1,1'). Sialic acid unit: 2.77 (broad, 1H, H-3e); 2.34 (nt, 1H, H-3a); 1.90 (s, 3H, NAc). Other unit: 7.58–7.20 (m, 4H, NBn); 4.22 (s, 2H, CH$_2$Ph); 3.42–3.18 (m, 12H, OCH$_2$CH$_2$O); 1.22 (s, 52H, CH$_2$); 0.85 (t, 6H, CH$_3$).

EXAMPLE 3

Synthesis of compound (5C),
O-(5-acetamido-3,5-dideoxy-D-glycero-α-D-galacto-2-nonulopyranosylonic
acid)-(2→3)-O-β-D-galactopyranosyl-(1→4)-[O-3-O-α-L-fucopyranosyl-β-D-glucopyranosyl]-(1→1)-11-O-para-(2-tetradecylhexadecanoyl)aminobenzyl-3,6,9-trioxaundecane-1,11-diol (Reaction Scheme 1)

3-1 Synthesis of compound (4C),
O-(methyl-5-acetamido-4,7,8,9-tetra-O-acetyl-3,5-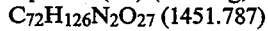dideoxy-D-glycero-α-D-galacto-2-nonulopyranosylonate)-(2→3)-O-(4-O-acetyl-2,6-di-O-benzoyl-β-D-galactopyranosyl)-(1→4)-[O-(2,3,4-tri-O-acetyl-α-L-fucopyranosyl)-(1→3)-O-2,6-di-O-benzoyl-β-D-glucopyranosyl]-(1→1)-11-O-para-(2-tetradecylhexadecanoyl)aminobenzyl-3,6,9-trioxaundecane-1,11-diol To a solution of compound (2A) (110 mg, 0.0651 mmol) and compound (3C) (96 mg, 0.131 mmol) in methylene chloride (3 ml) was added MS 4A AW300 (2 g), and the mixture stirred at room temperature for 40 min. To the resulting mixture cooled with ice, was added BF$_3$.OEt$_2$ (0.05 ml) and stirred for 5 hours. After completion of the reaction as confirmed by TLC (methylene chloride:methanol=30:1), the reaction solution was filtered through Celite, and combined filtrate and washings extracted with methylene chloride. The organic layer was washed with Na$_2$CO$_3$ and H$_2$O, dehydrated over Na$_2$SO$_4$, which was then separated by filtration, and the filtrate was concentrated under reduced pressure. The resulting syrup was subjected to column chromatography to give compound (4C) (108 mg, 73.5%) with an eluent (methylene chloride:methanol=35:1).

$C_{119}H_{164}N_2O_{40}$ (2262.595)

$[\alpha]_D = -2.2274$ (c 1.175, CHCl$_3$)

IR $\nu$ (film, max.) $cm^{-1}$: 3400–3150 (NH); 3150–2800 (CH); 1750 (ester); 1660, 1530 (amide); 710 (phenyl).

$^1$H NMR (300 MHz, CDCl$_3$): Fucose unit: 5.45 (d, 1H, $J_{1,2}=2.79$ Hz, H-1); 5.27 (m, 2H, H-2,5); 1.34 (d, 3H, $J_{5,6}=6.49$ Hz, Me). Lactose unit: 5.33 (dd, 1H, $J_{1,2}=8.61$ Hz, $J_{2,3}=9.44$ Hz, H-2); 5.27 (dd, 1H, $J_{1',2'}=8.09$ Hz, $J_{2',3'}=9.66$ Hz, H-2'); 5.12 (d, 1H, H-1'); 5.06 (d, 1H, $J_{3',4'}=2.99$ Hz, H-4'); 4.75 (dd, 1H, H-3'); 4.69 (m, 2H, H-6'); 4.49 (m, 1H, H-1); 4.47 (m, 1H, H-6); 4.26 (m, 1H, H-6); 4.12 (t, 1H, $J_{2,3}=J_{3,4}=9.39$ Hz, H-3); 3.93 (m, 1H, H-5'). Sialic acid unit: 5.63 (m, 1H, H-8); 5.25 (dd, 1H, $J_{6,7}=2.90$ Hz, $J_{7,8}=9.45$ Hz, H-7); 4.84 (m, 1H, H-4); 4.37 (dd, 1H, $J_{gem}=11.36$ Hz, H-9); 4.19 (dd, 1H, $J_{8,9'}=3.53$ Hz, H-9'); 3.76 (s, 1H, COOMe); 3.75 (m, 1H, H-5); 2.52 (dd, 1H, $J_{gem}=12.42$ Hz, $J_{3e,4}=4.45$ Hz, H-3e); 1.68 (t, 1H, H-3a). Other unit: 8.22–7.25 (m, 25H, 40 Bz, NHBn); 4.48 (s, 2H, CH$_2$Ph); 3.58–3.21 (m, 16H, OCH$_2$CH$_2$O); 2.20, 2.11, 2.05, 1.94, 1.88, 1.87, 1.75, 1.65, 1.43 (9 s, 27H, 80 Ac, NAc); 1.24 (s, 52H, CH$_2$); 0.88 (t, 6H, CH$_3$).

3-2 Synthesis of compound (5C),
O-(5-acetamido-3,5-dideoxy-D-glycero-α-D-galacto-2-nonulopyranosylonic
acid)-(2→3)-O-β-D-galactopyranosyl-(1→4)-[O-α-L-fucopyranosyl-(1→3)-O-β-D-glucopyranosyl]-(1→1)-11-O-para-(2-tetradecylhexadecanoyl)aminobenzyl-3,6,9-trioxaundecane-1,11-diol (Reaction Scheme 1)

To a solution of compound (4C) (104 mg, 0.0460 mmol) in methanol (5 ml) was added 28% sodium methoxide (10 drops), and the mixture stirred for 24 hours at 40° C. Then water (0.5 ml) was added and the mixture stirred for 10 hours. After completion of the reaction as confirmed by TLC (butanol:methanol:water=3:2:1), the reaction mixture was neutralized with ion exchange resin IR-120 (H+), which was then separated by filtration, and the filtrate was concentrated under reduced pressure. The resulting syrup was subjected to gel filtration with Sephadex LH-20 to give compound (5C) (64.6 mg, quantitative).

$C_{74}H_{130}N_2O_{28}$ (1495.840)

$[\alpha]_D = -22.229$ (c 1.050, chloroform:methanol:water=5:4:0.5)

IR $\nu$ (KBr, max.) $cm^{-1}$: 3700–2650 (NH, OH); 2920, 2850 (Me, methylene); 1730 (C=O); 1660, 1530 (amide).

$^1$H NMR (300 MHz, DMSO-D$_2$O): Fucose unit: 5.15 (d, 1H, $J_{1,2}=3.37$ Hz, H-1); 4.58 (m, 1H, H-5); 0.97 (d, 3H, $J_{5,6}=6.28$ Hz, Me). Lactose unit: 4.24 (m, 2H, H-1,1'). Sialic acid unit: 2.74 (broad, 1H, H-3e); 2.28 (nt, 1H, H-3a); 1.87 (s, 3H, NAc). Other unit: 7.53–7.14 (m, 4H, NBn); 4.36 (s, 2H, CH$_2$Ph); 3.23–3.14 (m, 16H, OCH$_2$CH$_2$O); 1.17 (s, 52H, CH$_2$); 0.79 (t, 6H, CH$_3$).

EXAMPLE 4

Synthesis of compound (5D),
O-(5-acetamido-3,5-dideoxy-D-glycero-α-D-galacto-2-nonulopyranosylonic
acid)-(2→3)-O-β-D-galactopyranosyl-(1→4)-[O-α-L-fucopyranosyl-(1→3)-O-β-D-glucopyranosyl]-(1→1)-5-O-para-(2-tetradecylhexadecanoyl)aminobenzyl-3,6,9,12-tetraoxatetradecane-1,14-diol 4-1 Synthesis of compound (4D),
O-(methyl-5-acetamido-4,7,8,9-tetra-O-acetyl-3,5-dideoxy-D-glycero-α-D-galacto-2-nonulopyranosylonate)-(2→3)-O-(4-O-acetyl-2,6-di-O-benzoyl-β-D-galactopyranosyl)-(1→4)-[3-O-(2,3,4-tri-O-acetyl-α-L-fucopyranosyl)-(1→3)-O-2,6-di-O-benzoyl-β-D-glucopyranosyl]-(1→1)-5-O-para-(2-tetradecylhexadecanoyl)aminobenzyl-3,6,9,12-tetraoxatetradecane-1,14-diol To a solution of compound (2A) (110 mg, 0.0651 mmol) and compound (3D) (101 mg, 0.130 mmol) in methylene chloride (3 ml) was added MS 4A AW300 (2 g), and the mixture stirred at room temperature for 1 hour. To the resulting mixture cooled with ice was added BF$_3$.OEt$_2$ (0.05 ml) and stirred for 5 hours. After completion of the reaction as confirmed by TLC (toluene:methanol=15:1), the reaction solution was filtered through Celite, and combined filtrate and washings extracted with methylene chloride. The organic layer was washed with Na$_2$CO$_3$ and H$_2$O, dehydrated over Na$_2$SO$_4$, which was then separated by filtration, and the filtrate was concentrated under reduced pressure. The resulting syrup was subjected to column chromatography to give compound (4D) (114 mg, 76.0%) with an eluent (ethyl acetate:hexane =4:1).

C$_{121}$H$_{168}$N$_2$O$_{41}$ (2306.648)

[α]$_D$= +8.9758 (c 1.990, CHCl$_3$)

IR ν (film, max.) cm$^{-1}$: 3400–3150 (NH); 3150–2700 (CH); 1750 (ester); 1660, 1530 (amide); 710 (phenyl).

$^1$H NMR (300 MHz, CDCl$_3$): Fucose unit: 5.45 (d, 1H, J$_{1,2}$=2.83 Hz, H-1); 5.30 (m, 2H, H-2,5); 1.34 (d, 3H, J$_{5,6}$=6.57 Hz, Me). Lactose unit: 5.33 (dd, 1H, J$_{1,2}$=7.78 Hz, J$_{2,3}$=9.58 Hz, H-2); 5.30 (dd, 1H, J$_{1',2'}$=8.17 Hz, J$_{2',3'}$=10.27 Hz, H-2'); 5.12 (d, 1H, H-1'); 5.06 (d, 1H, J$_{3',4'}$=3.50 Hz, H-4'); 4.75 (dd, 1H, H-3'); 4.70 (m, 2H, H-6'); 4.49 (d, 1H, H-1); 4.48 (dd, 1H, J$_{5,6}$=3.20 Hz, H-6); 4.26 (t, 1H, J$_{5,6}$=J$_{gem}$=9.48 Hz, H-6); 4.12 (t, 1H, J$_{2,3}$=J$_{3,4}$=9.40 Hz, H-3); 3.96 (m, 1H, H-5'). Sialic acid unit: 5.62 (m, 1H, H-8); 5.25 (dd, 1H, J$_{6,7}$=2.81 Hz, J$_{7,8}$=9.52 Hz, H-7); 4.84 (m, 1H, H-4); 4.37 (dd, 1H, J$_{8,9}$=2.01 Hz, J$_{gem}$=11.06 Hz, H-9); 4.19 (dd, 1H, J$_{8,9'}$=7.66 Hz, H-9'); 3.76 (s, 1H, COOMe); 3.75 (m, 1H, H-5); 3.50 (dd, 1H, J$_{5,6}$=11.10 Hz, H-6); 2.52 (dd, 1H, J$_{gem}$=12.46 Hz, J$_{3e,4}$=4.51 Hz, H-3e); 1.71 (t. 1H, H-3a). Other unit: 8.22–7.26 (m, 25H, 40 Bz, NHBn); 4.50 (s, 2H, CH$_2$Ph); 3.66–3.21 (m, 20H, OCH$_2$CH$_2$O); 2.20, 2.11, 2.05, 1.94, 1.88, 1.87, 1.75. 1.64, 1.43 (9 s, 27H, 80 Ac, NAc); 1.24 (s, 52H, CH$_2$); 0.88 (t, 6H, CH$_3$).

4-2 Synthesis of compound (5D),
O-(5-acetamido-3,5-dideoxy-D-glycero-α-D-galacto-2-nonulopyranosylonic acid)-(2→3)-O-β-D-galactopyranosyl-(1→4)-[O-α-L-fucopyranosyl-(1→3)]-O-β-D-glucopyranosyl]-(1→1)-5-O-para-(2-tetradecylhexadecanoyl)aminobenzyl-3,6,9,12-tetraoxatetradecane-1,14-diol (Reaction Scheme 1)

To a solution of compound (4D) (105 mg, 0.0455 mmol) in methanol (5 ml) was; added 28% sodium methoxide (15 drops), and the mixture stirred for 24 hours at 40° C. Then water (0.5 ml) was added and the mixture stirred for 10 hours. After completion of the reaction as confirmed by TLC (butanol:methanol:water=3:2:1), the reaction mixture was neutralized with ion exchange resin IR-120 (H+), which was then separated by filtration, and the filtrate was concentrated under reduced pressure. The resulting syrup was subjected to gel filtration with Sephadex LH-20 to give compound (5D) (70.1 mg, quantitative).

C$_{76}$H$_{134}$N$_2$O$_{29}$ (1539.893)

[α]$_D$= −44.711 (c 1.050, chloroform:methanol:water=5:4:0.5)

IR ν (KBr, max.) cm$^{-1}$: 3700–2650 (NH, OH); 2930, 2860 (Me, methylene); 1720 (C=O); 1650, 1530 (amide).

$^1$H NMR (300 MHz, DMSO-D$_2$O): Fucose unit: 5.15 (d, 1H, J$_{1,2}$=3.39 Hz, H-1); 4.58 (m, 1H, H-5); 0.98 (d, 3H, J$_{5,6}$=6.30 Hz, Me). Lactose unit: 4.24 (m, 2H, H-1,1'). Sialic acid unit: 2.73 (broad, 1H, H-3e); 2.27 (nt, 1H, H-3a); 1.87 (s, 3H, NAc). Other unit: 7.53–7.14 (m, 4H, NBn); 4.36 (s, 2H, CH$_2$Ph); 3.37–3.14 (m, 20H, OCH$_2$CH$_2$O); 1.17 (s, 52H, CH$_2$); 0.80 (t, 6H, CH$_3$).

EXAMPLE 5

5-1 Preparation of liposomes

A solution of 200 μg of phosphatidylcholine, 100 μg of cholesterol, 7.5 μg of dicetyl phosphate and 50 μg of a compound of the invention in a mixture of chloroform/methanol=2/1 (ca. 1 ml) was evaporated under reduced pressure to dryness followed by addition of 0.25 ml of a phosphate-buffered saline solution. The mixture was ultrasonicated (an output of 90 watts) for 5 min. and stirred (a vortex mixer) for 5 min. to form a liposome dispersion.

5-2 Experiment on the adhesion-inhibitory effect

Vascular endothelial cells of the normal human umbilical cord grown to confluence were stimulated in 24-well plates with 200 U/ml of recombinant interleukin 1β (called hereafter rhIL1β, manufactured by Genzyme) at 37° C. for 4 hours. After removal of the supernatant by suction, liposome dispersions each prepared from a compound of the invention in an amount of 20 μg/ml equivalent were added except for the rhIL1β-untreated group (sample 1) and the treated groups (samples 2 and 3). The mixtures were then allowed to react at room temperature for 30 min. Subsequently, promyelocytic leukemia cell line HL-60 with 2',7'-bis(-carboxyethyl)-5,6-carboxyfluorescene acetoxymethyl ester fluorescent dye enclosed was added at a level of 1×10$^6$ cells per well followed by centrifugal operation at 100 rpm for 20 min. Each well was washed three times followed by addition of 0.5 ml of 0.5% Triton X-100 and stirring. The contents were divided into 100 μl portions in 96-well plates and measurement was made on a Baxter fluorometer at 485 nm/535 nm.

5-3 Preparation of samples

1: rhIL1β-untreated group
2: rhIL1β-treated group
3: rhIL1β-treated group+compound-free liposome dispersion-treated group
4: rhIL1β-treated group+compound 5A-containing liposome dispersion-treated group (2EG)*
5: rhIL1β-treated group+compound 5B-containing liposome dispersion-treated group (3EG)*
6: rhIL1β-treated group+compound 5C-containing liposome dispersion-treated group (4EG)*
7: rhIL1β-treated group+compound 5D-containing liposome dispersion-treated group (5EG)*

* 2EG, 3EG, 4EG or 5EG represents a compound of the invention containing 2, 3, 4 or 5 CH$_2$CH$_2$O units, respectively. The same shall apply hereinafter.

Amount adhered and % inhibition of adhesion of HL-60 cells as measured from fluorescence intensity are shown in Table 1 below.

% Inhibition of adhesion=100−[(fluorescence intensity for rhIL1β-treated group+compound-free or a compound-containing liposome dispersion-treated group)−(fluorescence intensity for rhIL1β-untreated group)/(fluorescence intensity for rhIL1β-treated group−fluorescence intensity for rhIL1β-untreated group)]×100

TABLE 1

| 1 | 2 | 3 | 4 | 5 | 6 | 7 |
|---|---|---|---|---|---|---|
| Amount of HL-60 cancer cells adhered (fluorescence intensity) | | | | | | |
| 1295 | 108934 | 111704 | 22769 | 17957 | 26907 | 17405 |
| % Inhibition of adhesion | | | | | | |

TABLE 1-continued

| 1 | 2 | 3 | 4 | 5 | 6 | 7 |
|---|---|---|---|---|---|---|
| — | — | −2.57 | 80.04 | 84.52 | 76.20 | 85.03 |

5-4 Comparison in adhesion-inhibitory effect between 2→3 sialyl Le$^x$ (natural type) and the compounds of the invention Vascular endothelial cells of the normal human umbilical cord grown to confluence were stimulated in 24-well plates with 200 U/ml of rhIL1$\beta$ at 37° C. for 4 hours. After removal of the supernatant by suction liposome dispersions each prepared from 2→3 sialyl Le$^x$ or a compound of the invention in an amount of 11.8 $\mu$M equivalent were added except for the rhIL1$\beta$-untreated and treated groups. The mixtures were then allowed to react at room temperature for 30 min. Subsequently, colon carcinoma cell line Colo 201 with 2',7'-bis-(carboxyethyl)-5,6-carboxyfluorescene acetoxymethyl ester fluorescent dye enclosed was added at a level of 1×10$^6$ cells per well followed by centrifugal operation at 100 rpm for 20 min. Each well was washed three times followed by addition of 0.5 ml of 0.5% Triton X-100 and stirring. The contents were divided into 100 $\mu$l portions in 96-well plates and measurement was made on a Baxter fluorometer at 485 nm.

5-5 Preparation of samples

1: rhIL1$\beta$-untreated group
2: rhIL1$\beta$-treated group
3: rhIL1$\beta$-treated group+compound-free liposome dispersion-treated group
4: rhIL1$\beta$-treated group+2→3 sialyl Le$^x$-containing liposome dispersion-treated group
5: rhIL1$\beta$-treated group+compound 5E-containing liposome dispersion-treated group (OEG)*
6: rhIL1$\beta$-treated group+compound 5A-containing liposome dispersion-treated group (2EG)
7: rhIL1$\beta$-treated group+compound 5B-containing liposome dispersion-treated group (3EG)
8: rhIL1$\beta$-treated group+compound 5C-containing liposome dispersion-treated group (4EG)
9: rhIL1$\beta$-treated group+compound 5D-containing liposome dispersion-treated group (5EG)

* OEG represents a control compound containing no CH$_2$CH$_2$O unit. The same shall apply hereinafter.

Amount adhered and % inhibition of adhesion of Colo 201 cancer cells as measured from fluorescence intensity are shown in Table 2 below.

TABLE 2

| Amount of Colo 201 cells adhered (fluorescence intensity) | | | | | |
|---|---|---|---|---|---|
| 1 | 2 | 3 | 4 | 5 | 6 |
| 42432 | 654549 | 623616 | 448512 | 595253 | 246293 |
| 7 | 8 | 9 | | | |
| 212789 | 240330 | 240554 | | | |

| % Inhibition of adhesion | | | | | | | | |
|---|---|---|---|---|---|---|---|---|
| 1 | 2 | 3 | 4 | 5 | 6 | 7 | 8 | 9 |
| — | — | 5.05 | 33.65 | 9.68 | 66.69 | 72.16 | 67.66 | 67.63 |

The 2→3 sialyl Le$^x$ (natural type) used in this experiment is represented by the following formula

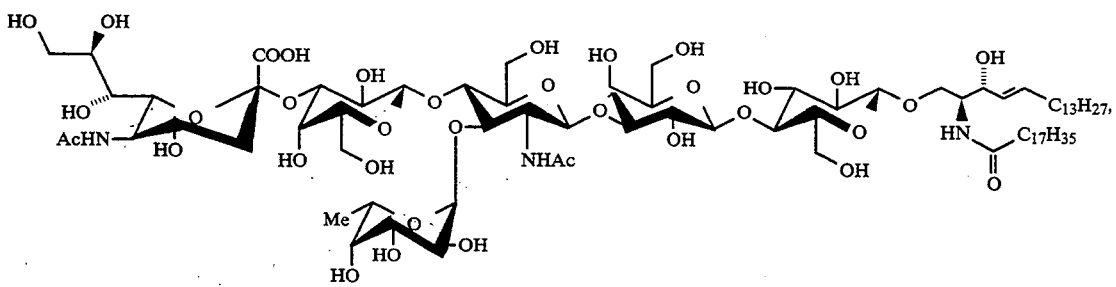

which was prepared according to the method described in Kameyama A. et al., Journal of Carbohydrate Chemistry, 10, 549–560, 1991.

Compound 5E (OEG) used in this experiment and Examples 6 and 8 is para-(2-tetradecylhexadecanoyl)-aminobenzyl-O-(5-acetamido-3,5-dideoxy-D-glycero-$\alpha$-D-galacto-2-nonulopyranosylonic acid)-(2→3)-O-$\beta$-galactopyranosyl-(1→4)-[O-$\alpha$-L-fucopyranosyl-(1→3)-$\beta$-D-glucopyranoside]represented by the formula

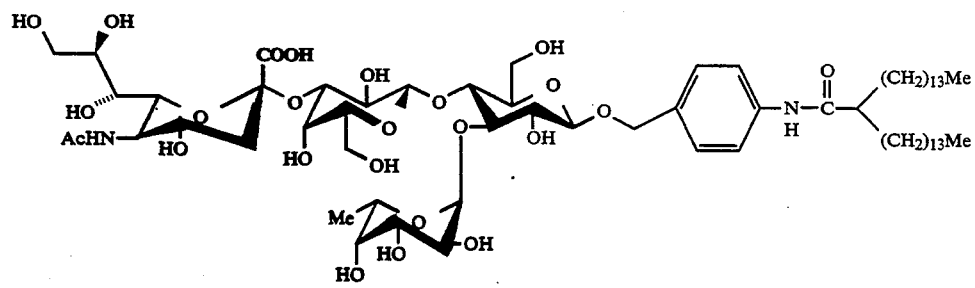

and has the following physical properties:
C$_{66}$H$_{114}$N$_2$O$_{24}$ (1319.626)

[$\alpha$]$_D$=−43.040 (c 0.810, chloroform:methanol:water=5:4:0.7)

IR $\nu$ (KBr, max) cm$^{-1}$: 3700–3000 (NH, OH); 2920, 2850 (Me, methylene); 1660, 1530 (amide).

$^1$H NMR (300 MHz, DMSO-D$_2$O): Fucose unit: 5.17 (d, 1H, J$_{1,2}$=3.76 Hz, H-1); 4.61 (m, 1H, H-5); 1.00 (d, 3H, J$_{5,6}$=6.48 Hz, Me). Lactose unit: 4.32 (m, 2H, H-1,1'). Sialic acid unit: 2.60 (broad, 1H, H-3e); 2.33 (nt, 1H, H-3a); 1.87 (s, 3H, NAc). Other unit: 7.56, 7.29 (dd, 4H, J=8.5 Hz, NBn); 4.52, 4.74 (dd, 2H, J=12.1 Hz, CH$_2$Ph); 1.22 (s, 52H, CH$_2$); 0.85 (t, 6H, CH$_3$).

EXAMPLE 6

6-1 Preparation of oily emulsion

A mixed solution of 6 mg of egg yolk lecithin (manufactured by Nacalaitesque Inc.), 30 μl of soybean oil J. P. (manufactured by Yoshida Seiyaku), 470 μl of distilled water for injection (manufactured by Otsuka Seiyaku) and 125 μg of a compound of the invention was ultrasonicated (an output of 90 watts) for 10 min. to prepare an oily emulsion. The oily emulsion was further passed through a polycarbonate membrane filter having 0.2 μm average pore diameter (manufactured by Millipore) to provide an average particle size of 0.2 μm.

6-2 Experiment on the adhesion-inhibitory effect

Vascular endothelial cells of the normal human umbilical cord grown to confluence were stimulated in 24-well plates with 200 U/ml of rhIL1$\beta$ at 37° C. for 4 hours. After removal of the supernatant by suction, oily emulsions each prepared from a compound of the invention in an amount of 20 μg/ml equivalent were added except for the rhIL1$\beta$-untreated group (sample 1) and the treated groups (samples 2 and 3). The mixtures were then allowed to react at room temperature for 30 min. Subsequently, promyelocytic leukemia cell line HL-60 with 2′,7′-bis(carboxyethyl)-5,6-carboxyfluorescene acetoxymethyl ester fluorescent dye enclosed was added at a level of $1 \times 10^6$ cells per well followed by centrifugal operation at 100 rpm for 20 min. Each well was washed three times followed by addition of 0.5 ml of 0.5% Triton X-100 and stirring. The contents were divided into 100 μl portions in 96-well plates and measurement was made on a Baxter fluorometer at 485 nm/535 nm.

6-3 Preparation of samples

1: rhIL1$\beta$-untreated group
2: rhIL1$\beta$-treated group
3: rhIL1$\beta$-treated group+compound-free oily emulsion dispersion-treated group
4: rhIL1$\beta$-treated group+2→3 sialyl Lewis X (natural type)-containing oily emulsion dispersion-treated group
5: rhIL1$\beta$-treated group+compound 5E-containing oily emulsion dispersion-treated group (OEG)
6: rhIL1$\beta$-treated group+compound 5A-containing oily emulsion dispersion-treated group (2EG)
7: rhIL1$\beta$-treated group+compound 5B-containing oily emulsion dispersion-treated group (3EG)
8: rhIL1$\beta$-treated group+compound 5C-containing oily emulsion dispersion-treated group (4EG)
9: rhIL1$\beta$-treated group+compound 5D-containing oily emulsion dispersion-treated group (5EG)

Amount adhered and % inhibition of adhesion of HL-60 cancer cells as measured from fluorescence intensity are shown in Table 3 below.

% inhibition of adhesion = 100 − [(fluorescence intensity for rhIL1$\beta$-treated group+compound-free or a compound-containing oily emulsion dispersion-treated group) − (fluorescence intensity for rhIL1$\beta$-untreated group)/(fluorescence intensity for rhIL1$\beta$-treated group − fluorescence intensity for rhIL1$\beta$-untreated group)] × 100

TABLE 3

| 1 | 2 | 3 | 4 | 5 | 6 | 7 | 8 | 9 |
|---|---|---|---|---|---|---|---|---|
| Amount of HL-60 cancer cells adhered (fluorescence intensity) ||||||||||
| 228 | 37638 | 35803 | 16869 | 24307 | 13287 | 6439 | 6762 | 2782 |
| % Inhibition of adhesion |||||||||
| — | — | 4.9 | 55.5 | 35.6 | 65.3 | 83.4 | 82.5 | 93.2 |

EXAMPLE 7

7-1 Preparation of liposomes

A solution of 200 μg of phosphatidylcholine, 100 μg of cholesterol, 7.5 μg of dicetyl phosphate and 50 μg of a compound of the invention in a mixture of chloroform/methanol=2/1 (ca. 1 ml) was evaporated under reduced pressure to dryness followed by addition of 0.25 ml of a phosphate-buffered saline solution. The mixture was ultrasonicated (an output of 90 watts) for 5 min. and stirred (a vortex mixer) for 5 min. to form a liposome dispersion.

7-2 Experiment on the adhesion-inhibitory effect

Vascular endothelial cells of the normal human umbilical cord grown to confluence were stimulated in 24-well plates with 200 U/ml of rhIL1$\beta$ at 37° C. for 4 hours. After removal of the supernatant by suction, liposome dispersions each prepared from a compound of the invention in an amount of 20 μg/ml equivalent were added except for the rhIL1$\beta$-untreated group (sample 1) and the treated groups (samples 2 and 3). The mixtures were then allowed to react at room temperature for 30 min. Subsequently, human normal lymphocytes with 2′,7′-bis-(carboxyethyl)-5,6-carboxyfluorescene acetoxymethyl ester fluorescent dye enclosed was added at a level of $2 \times 10^6$ cells per well followed by centrifugal operation at 100 rpm for 20 min. Each hole was washed three times followed by addition of 0.5 ml of 0.5% Triton X-100 and stirring. The contents were divided into 100 μl portions in 96-well plates and measurement was made on a Baxter fluorometer at 485 nm/535 nm.

7-3 Preparation of samples

1: rhIL1$\beta$-untreated group
2: rhIL1$\beta$-treated group
3: rhIL1$\beta$-treated group+compound-free liposome dispersion-treated group
4: rhIL1$\beta$-treated group+compound 5A-containing liposome dispersion-treated group (2EG)
5: rhIL1$\beta$-treated group+compound 5B-containing liposome dispersion-treated group (3EG)
6: rhIL1$\beta$-treated group+compound 5C-containing liposome dispersion-treated group (4EG)
7: rhIL1$\beta$-treated group+compound 5D-containing liposome dispersion-treated group (5EG)

Amount adhered and % inhibition of adhesion of human normal lymphocytes as measured from fluorescence intensity are shown in Table 4 below.

TABLE 4

| 1 | 2 | 3 | 4 | 5 | 6 | 7 |
|---|---|---|---|---|---|---|
| Amount of human normal lymphocytes adhered (fluorescence intensity) |||||||
| 5 | 18084 | 19986 | 6882 | 6993 | 10513 | 8817 |
| % Inhibition of adhesion |||||||
| — | — | −10.5 | 61.9 | 61.3 | 41.9 | 51.3 |

EXAMPLE 8

8-1 Preparation of oily emulsion

A mixed solution of 6 mg of egg yolk lecithin (manufactured by Nacalaitesque Inc.), 30 μl of soybean oil J. P. (manufactured by Yoshida Seiyaku), 470 μl of distilled water for injection (manufactured by Otsuka Seiyaku) and 125 μg of a compound of the invention was ultrasonicated (an output of 90 watts) for 10 min. to prepare an oily emulsion. The oily emulsion was further passed through a polycarbonate membrane filter having 0.2 μm average pore diameter (manufactured by Millipore) to provide an average particle size of 0.2 μm.

8-2 Experiment on the adhesion-inhibitory effect

Vascular endothelial cells of the normal human umbilical cord grown to confluence were stimulated in 24-well plates with 200 U/ml of rhIL1ββ at 37° C. for 4 hours. After removal of the supernatant by suction, oily emulsions each prepared from a compound of the invention in an amount of 20 μg/ml equivalent were added except for the rhIL1β-untreated (Sample 1) and treated groups (Samples 2 and 3). The mixtures were then allowed to react at room temperature for 30 min. Subsequently, human normal lymphocytes with 2′,7′-bis(carboxyethyl)-5,6-carboxyfluorescence acetoxymethyl ester fluorescent dye enclosed was added at a level of 2×10⁶ cells per well followed by centrifugal operation at 100 rpm for 20 min. Each well was washed three times followed by addition of 0.5 ml of 0.5% Triton X-100 and stirring. The contents were divided into 100 μl portions in 96-well plates and measurement was made on a Baxter fluorometer at 485 nm/535 nm.

8-3 Preparation of samples

1: rhIL1β-untreated group
2: rhIL1β-treated group
3: rhIL1β-treated group+compound-free oily emulsion dispersion-treated group
4: rhIL1β-treated group+2→3 sialyl Lewis X-containing oily emulsion dispersion-treated group
5: rhIL1β-treated group+compound 5E-containing oily emulsion dispersion-treated group (OEG)
6: rhIL1β-treated group+compound 5A-containing oily emulsion dispersion-treated group (2EG)
7: rhIL1β-treated group+compound 5B-containing oily emulsion dispersion-treated group (3EG)
8: rhIL1β-treated group+compound 5C-containing oily emulsion dispersion-treated group (4EG)
9: rhIL1β-treated group+compound 5D-containing oily emulsion dispersion-treated group (5EG)

Amount adhered and percent inhibition of adhesion of human normal lymphocytes as measured from fluorescence intensity are shown in Table 5 below.

TABLE 5

| 1 | 2 | 3 | 4 | 5 | 6 | 7 | 8 | 9 |
|---|---|---|---|---|---|---|---|---|
| Amount adhered (fluorescence intensity) | | | | | | | | |
| 856 | 26944 | 21503 | 9320 | 14781 | 9773 | 10045 | 13563 | 10324 |
| % Inhibition of adhesion | | | | | | | | |
| — | — | 20.9 | 67.6 | 46.6 | 65.8 | 64.8 | 51.3 | 63.7 |

What is claimed is:

1. A glycolipid derivative of formula (I)

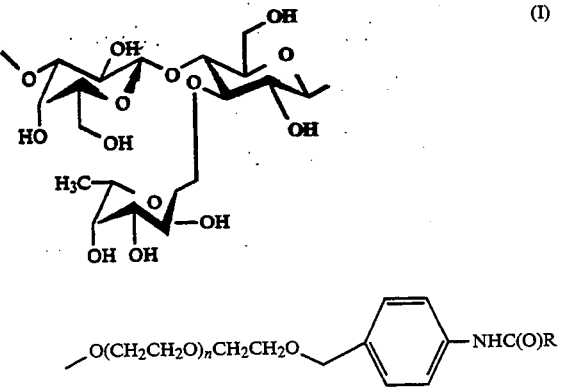

wherein X is selected from the group consisting of

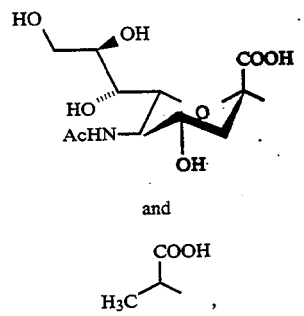

and

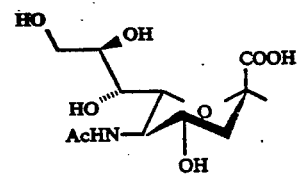

n is 0 or an integer from 1–10, and R is a branched hydrocarbon chain containing from 19 to 39 carbon atoms, or a pharmaceutically acceptable salt thereof.

2. A glycolipid derivative of claim 1 wherein X is

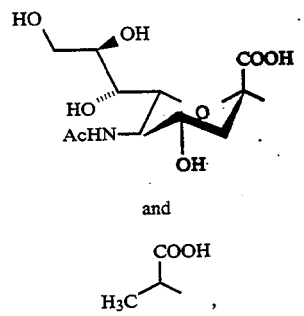

3. A glycolipid derivative of claim 1 wherein X is

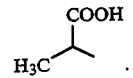

4. A pharmaceutical composition which comprises a glycolipid derivative of claim 1 or a pharmaceutically acceptable salt thereof as an active ingredient and a pharmaceutically acceptable carrier.

5. A method of treating inflammation which comprises administering to a patient in need thereof a pharmaceutically effective amount of the composition of claim 4.

* * * * *